US012122729B2

(12) United States Patent
Zhang et al.

(10) Patent No.: US 12,122,729 B2
(45) Date of Patent: *Oct. 22, 2024

(54) PEROVSKITE-TYPE COMPOUNDS OF FORMULA ABX3

(71) Applicant: XI'AN CRYSTEN MATERIALS TECHNOLOGY CORPORATION LIMITED, Xi'an (CN)

(72) Inventors: Weixiong Zhang, Guangzhou (CN); Shaoli Chen, Guangzhou (CN); Xiaoming Chen, Guangzhou (CN)

(73) Assignee: XI'AN CRYSTEN MATERIALS TECHNOLOGY CORPORATION LIMITED, Xi'an (CN)

( * ) Notice: Subject to any disclaimer, the term of this patent is extended or adjusted under 35 U.S.C. 154(b) by 866 days.

This patent is subject to a terminal disclaimer.

(21) Appl. No.: 17/132,109

(22) Filed: Dec. 23, 2020

(65) Prior Publication Data

US 2021/0269375 A1    Sep. 2, 2021

Related U.S. Application Data

(63) Continuation-in-part of application No. 16/099,486, filed as application No. PCT/CN2017/097136 on Aug. 11, 2017, now Pat. No. 10,913,693.

(30) Foreign Application Priority Data

Aug. 12, 2016  (CN) .......................... 201610665880.3

(51) Int. Cl.
| | | |
|---|---|---|
| C07D 241/04 | (2006.01) | |
| C06B 29/22 | (2006.01) | |
| C06B 43/00 | (2006.01) | |
| C06B 45/00 | (2006.01) | |
| C06D 5/04 | (2006.01) | |
| C07D 241/12 | (2006.01) | |
| C07D 295/027 | (2006.01) | |
| C07D 487/08 | (2006.01) | |

(52) U.S. Cl.
CPC .............. *C06B 29/22* (2013.01); *C06B 43/00* (2013.01); *C06B 45/00* (2013.01); *C06D 5/04* (2013.01); *C07D 241/12* (2013.01); *C07D 295/027* (2013.01); *C07D 487/08* (2013.01)

(58) Field of Classification Search
CPC ........................... C07D 241/04; C07D 487/08
USPC .................................................. 544/349, 358
See application file for complete search history.

(56) References Cited

U.S. PATENT DOCUMENTS 4,552,598 A    11/1985  Lee et al.

FOREIGN PATENT DOCUMENTS

| CN | 101570459 A | 11/2009 |
|---|---|---|
| CN | 103396281 A | 11/2013 |
| CN | 104733617 A | 6/2015 |
| CN | 105514276 A | 4/2016 |
| CN | 105777458 A | 7/2016 |
| CN | 106278771 A | 1/2017 |
| JP | 2005-179168 A | 7/2005 |
| RU | 99122472 A | 9/2001 |
| RU | 2522611 C2 | 4/2012 |
| WO | 98/36938 A2 | 8/1998 |
| WO | 2014/191767 A1 | 12/2014 |
| WO | 2016/113321 A1 | 7/2016 |
| WO | 2018028685 A1 | 2/2018 |

OTHER PUBLICATIONS

Communication dated Jun. 23, 2021 from the European Patent Office in Application No. 17 838 815.3.
Communication dated Apr. 7, 2021 from the Canadian Intellectual Property Office in Application No. 3,027,813.
Search Report dated Jun. 8, 2021 in Brazilian Application No. 112018075493-5.
Communication dated Mar. 9, 2023 of Brazilian Patent Application No. 112018075493-5.
Communication dated Aug. 16, 2023 of Brazilian Patent Application No. 112018075493-5.
Communication dated Aug. 16, 2021 of Israeli Patent Application No. 262549.
Communication dated Feb. 3, 2021 from the Indian Intellectual Property Office in Application No. 201937008947.
Communication dated Feb. 24, 2023 in Vietnamese Application No. 1-2019-01206.
Communication dated Mar. 19, 2021 in Russian Application No. 2020120843/05(035602).
Communication dated Dec. 14, 2021 from the Japanese Patent Office in Application No. 2020-177516.
Communication dated May 25, 2022 of Israeli Patent Application No. 288380.
Dorwald, F. Zaragoza. Side Reactions in Organic Synthesis: A Guide to Successful Synthesis Design, Weinheim: WILEY-VCH Verlag Gmbh & Co. KGaA, 2005, Preface.
Shenghua Li et al., "3D Energetic Metal-Organic Frameworks: Synthesis and Properties of High Energy Materials", Angew. Chem., 2013, pp. 14281-14285, vol. 125.

(Continued)

*Primary Examiner* — Douglas M Willis
(74) *Attorney, Agent, or Firm* — Sughrue Mion, PLLC

(57) ABSTRACT

The present application belongs to the field of compounds, and particularly relates to the perovskite-type compound $ABX_3$. As a finding of the present application, the structural characteristics of the perovskite type enables the type of compound to be highly stable, thus overcoming the unsafety of an explosive having poor stability in the prior art. Meanwhile, the structural characteristics of the compound, such as rich energetic ligands, as well as the alternately arranged oxidizing energetic anions and reducing organic cations in the space, endow the compound with excellent performance on instantaneously releasing energy at detonation. The resulting three-dimensional structure allows the compound to not only have an energetic material effect but also overcome shortcomings of some existing energetic materials.

20 Claims, 13 Drawing Sheets

(56) References Cited

OTHER PUBLICATIONS

Oleksandr S. Bushuyev et al., "Metal-Organic Frameworks (MOFs) as Safer, Structurally Reinforced Energetics", Chem. Eur. J., 2013, pp. 1706-1711, vol. 19.
Jai Prakash Agrawal, "High Energy Materials: Propellants, Explosives and Pyrotechnics", Wiley-VCH Press, 2010, 495 pages.
Zhang Huazhu et al., "The Study of Explosives", Beijing: Ordnance Industry Press, 2004, p. 3.
Zhi Min Jin et al., "Diazabicyclo[2.2.2]octane-1,4-diium occluded in cubic anionic coordinated framework: the role of trifurcated hydrogen bonds of N-H•••O and C-H•••O", Journal of Molecular Structure, 2003, pp. 67-72, vol. 660.
Oleksandr S. Bushuyev et al., "Ionic Polymers as a New Structural Motif for High-Energy-Density Materials", J. Am. Chem. Soc., 2012, pp. 1422-1425, vol. 134.
Yuan Wang et al., "A Simple Method for the Prediction of the Detonation Performances of Metal-Containing Explosives", J. Phys. Chem. A., 2014, pp. 4575-4581, vol. 118.
Huabin Zhang et al., "A Highly Energetic N-Rich Metal-Organic Framework as a New High-Energy-Density Material", Chem. Eur. J., 2016, pp. 1141-1145, vol. 22.
Office Action for corresponding CN 201610665880.3, dated Apr. 18, 2017.
Office Action for corresponding TW 106127384, dated Jul. 2, 2018.
International Search Report for PCT/CN2017/097136, dated Sep. 30, 2017.
English translation of 1st OA dated Apr. 18, 2017 for corresponding CN application No. 201610665880.3 (of record).
English translation of 1st OA dated Jul. 2, 2018 for corresponding TW application No. 106127384 (of record).
1st OA for corresponding AU application No. 2017311153 dated Dec. 6, 2018.
1st OA for corresponding KR application No. 10-2018-7030235 dated Mar. 22, 2019.
English translation of Claims 1-6 of CN104733617A (of record) cited in CN 1st OA of CN Application No. 201610665880.3.
English translation of p. 2 of the specification of CN105514276A (of record) cited in CN 1st OA Appl'n No. 201610665880.3.
English translation of Claim 1 of CN105777458A (of record) cited in TW 1st OA Appl'n No. 106127384 and KR 1st OA Appl'n No. 10-2018-7030235.
M.A. Ilyushin, et al., Development of components of high-energy compositions, Monograph, Pushkin Leningrad State University, St .- Pb., 2006, pp. 55-71, 74, 78-79, 97-99, and 101-104.
P. E. Eaton, et al., Polynitrocubanes: Advanced High-Density, High-Energy Materials, WILEY-VCH Verlag GmbH, Weinheim, Fed. Rep. of Germany, 2000, vol. 12, Issue 15, Aug. 2, pp. 1143-1148.
Xiangyu Liu, et al., Environmentally friendly high-energy MOFs: crystal structures, thermostability, insensitivity and remarkable detonation performances, Journal Green Chemistry, 2015, Issue 2, vol. 17, p. 831-836.

Office Action issued Jun. 13, 2019 in corresponding Russian Patent Application No. 2018131394/05 with translation.
Search Report issued in counterpart Russian Patent Application No. 2018131394/05(051208) Jun. 7, 2019.
Office Action issued Jul. 31, 2019 in counterpart Chinese Patent Application No. 201710758276.X with translation.
Office Action issued Jul. 31, 2019 in counterpart Chinese Patent Application No. 201710758895.9 with translation.
Office Action issued Jul. 19, 2019 in counterpart Chinese Patent Application No. 201710757734.8 with translation.
Shaoli Chen et al., "A Class of High Latent Heat Three-Dimensional Perovskite-Type Compounds: [H14C6N2][M(ClO4)3] (M = Na/K/Rb)", Proceedings of the 9th National Conference on Inorganic Chemistry of Chinese Chemical Society-B: Coordination Chemistry, p. 305.
D.-f. Lu et al., Solar Energy Materials & Solar Cells, 114 (2013), pp. 1-8.
C.-F. Gao et al., Solar Energy Materials & Solar Cells, 128 (2014), pp. 221-230.
W.J. Xu et al., "Structural Phase Transitions in Perovskite Compounds Based on Diatomic or Multiatomic Bridges", CrystEngComm, 2016, 18, pp. 7915-7928.
G.-Z. Liu et al., "A Novel Molecular Cubic Perovskite Built From Charge-Assisted Hydrogen Bond Linkages" Synth. React. Inorg. M., 2011, 41, pp. 1091-1094.
First Non-Final Notice of Reasons for Rejection, dated Oct. 8, 2019, from the Japanese Patent Office in counterpart application No. 2018-546038.
Second Non-Final Notice of Reasons for Rejection, dated Feb. 12, 2020, from the Japanese Patent Office in counterpart application No. 2018-546038.
Communication dated Nov. 20, 2019, from the European Patent Office in counterpart application No. 17838815.3.
2nd Office Action, dated Dec. 13, 2019, from the Russian Patent and Trademark Office in counterpart application No. 2018131394/05.
Examination Report, dated Dec. 30, 2019, from the Intellectual Property Office of India in counterpart application No. 201937008947.
Office Action, dated Jan. 30, 2020, from the Canadian Intellectual Property Office in counterpart application No. 3027813.
2nd Office Action of divisional application, dated Mar. 9, 2020, from the State Intellectual Property Office of the P.R.C in counterpart application No. 201710758276.X.
2nd Office Action of divisional application, dated Mar. 9, 2020, from the State Intellectual Property Office of the P.R.C in counterpart application No. 201710758895.9.
Examination Report of divisional application, dated Feb. 21, 2020, from the Australian Patent Office in counterpart application No. 2019232800.
First Non-Final Office Action of the divisional application of the Taiwanese counterpart application (Application No. TW108119202) Apr. 7, 2020.
Second Non-Final Office Action of the divisional application of the Taiwanese counterpart application (Application No. TW108119202) Jul. 24, 2020.
First Technical Examination Report of Brazilian patent application 122023024836-8 dated Feb. 19, 2024.

PEROVSKITE-TYPE COMPOUNDS OF FORMULA ABX3

CROSS REFERENCE TO RELATED APPLICATIONS

This application is a continuation-in-part of U.S. application Ser. No. 16/099,486, filed Nov. 7, 2018, which is a National Stage of International Application No. PCT/CN2017/097136, filed Aug. 11, 2017, and which claims the benefit of priority based on Chinese Patent Application No. 201610665880.3 filed Aug. 12, 2016, the contents of all of which are incorporated herein by reference in their entireties.

BACKGROUND OF THE INVENTION

(1) Field of the Invention

The present application relates to the technical field of materials, and more particularly relates to perovskite type compounds.

(2) Description of Related Art

Energetic compound is a type of explosives with high energy density. The black powder, which is the first known energetic material discovered by ancient Chinese in the ninth century, is prepared by mixing sulfur, potassium nitrate, and charcoal powder, and has poor effect and unstable performance. In modern times, nitroglycerin, which had initially been discovered as a medicinal product, was found to be a high explosive later in manufacturing. Although nitroglycerin demonstrates much better performance in comparison to black powder, it is very dangerous for production and transportation due to its high sensibility. Through unremitting manufacturing and research, Alfred Bernhard Nobel found that diatomite can adsorb nitroglycerin, which, at the expense of certain explosive performance, can effectively improve the safety of products. Thus, nitroglycerin was successfully applied to industrial application. Nowadays, explosives with higher performance than nitroglycerin have been discovered and put into use one after another. The well-known trinitrotoluene (TNT) and the organic energetic materials such as cyclotrimethylene trinitramine (RDX) and cyclotetramethylene tetranitramine (HMX), which have a high detonation performance in comparison to TNT, are widely used in weapons and ammunition around the world. In recent years, the industrialization process of hexanitrohexaazaisowurtzitane (CL-20), an organic explosive with high performance, high cost and complicated procedures, has been explored by Chinese scientists, which has promoted the prospect of upgrading the military ammunition in China. In recent years, some metal-organic frameworks containing energetic organic ligands (e.g. *Angew. Chem. Int. Ed.* 2013, 52, 14031; *Chem. Eur. J.* 2013, 19, 1706) have attracted growing attention. With rich ligand adjustability and high detonation performance indicated by theoretical calculations, such energetic metal-organic frameworks are regarded as an important direction for the development of next-generation explosives.

In the course of modern explosive development, different explosives have demonstrated improved properties in different aspects, but are also inevitably accompanied by some defects of their own. For example, explosive potassium perchlorate was once used as the pro-oxidant for flash bombs, but it was eventually abandoned due to its high impact sensitivity which makes it prone to explosion in transit (see "High Energy Materials: Propellants, Explosives and Pyrotechnics", p. 347, edited by Jai Prakash Agrawal, Wiley-VCH Press, 2010). Among existing organic energetic materials as well as metal-organic framework energetic materials which are still in the stage of fundamental research, it is not rare to find those that have excellent detonation performance, but most of them are difficult to apply due to disadvantages of complicated synthetic processes, numerous steps, high cost, and poor stability, as well as high impact and friction sensitivities. Therefore, how to design and synthesize insensitive high-energetic materials with the advantages of low cost, high energy density and low sensitivity (high safety) is an everlasting pursuit in the field of energetic materials.

BRIEF SUMMARY OF THE INVENTION

A first objective of the present application is to provide a sort of novel energetic materials.

A second objective of the present application is to provide a sort of novel energetic materials with high safety.

A third objective of the present application is to provide a sort of novel energetic materials with high detonation performance.

A fourth objective of the present application is to provide a sort of novel energetic materials with a high energy density.

In the field of energetic materials, the present application takes perovskite type compounds as energetic material for the first time, and makes a breakthrough and finds that the perovskite type compound is particularly suitable to be used as the energetic material.

The said perovskite type compound has an energetic group, such as a $ClO_4^-$ energetic group. This type of energetic material may be used as, but not limited to an explosive. For example, this material further may be used as a propellant, rocket fuel or a gas generant of safety air bags.

The perovskite type compound is a solid compound having same type of crystal structure as calcium titanate ($CaTiO_3$). They have the same chemical general formula $ABX_3$, where A and B are cations of different sizes, and X is an anion. An ideal structure is a high-symmetric cubic structure, and the structural features may be described as follows: each B-site cation is connected with six adjacent X anions, and each X anion is connected with two adjacent B-site cations, thereby forming a three-dimensional anionic framework consisting of cubic cage units. Cavities of these cubic cage units are filled with the A-site cations. A is at least one cation, B is at least one cation, and X is at least one anion. When perovskite includes more than one A cations, different A cations may be distributed at A sites in an ordered or disordered manner. When the perovskite includes more than one B cations, different B cations may be distributed at B sites in an ordered or disordered manner. When the perovskite includes more than one X anions, different X anions may be distributed at X sites in an ordered or disordered manner.

At present, perovskite type compounds are generally studied and applied as ferroelectric materials, photoelectric materials, electromagnetic materials, etc.

As a finding of the present application, a three-dimensional structure is formed in perovskite type compound in which cation A is larger than cation B, and X is the energetic anionic group. In addition to endowing the compound with the effects of energetic materials, such a structure can also enable the compound to overcome some defects in existing energetic materials. For example, as the inventor speculates, the structural characteristics of perovskite type compound provide the compound with high stability, so as to overcome the unsafety of explosives having poor stability in the prior art; in addition, the structural characteristics of the compound, such as rich energetic groups, as well as alternately arranged oxidizing energetic anions and reducing organic cations in the space, endow the compound with excellent performance on instantaneously releasing energy at detonation. Low sensitivity in storage and instantaneous burst at detonation, these two seemingly contradictory characteristics are integrated due to the three-dimensional spatial structural characteristics of perovskite type compounds, which enables the compound to be particularly suitable for being used as energetic materials such as insensitive high-energetic explosives.

An energetic ligand refers to an explosive ligand. However, not all compounds containing explosive ligands are explosive; whether or not a compound is explosive depends on its entire molecular structure rather than on a single ligand (see The Study of Explosives, p. 3, Zhang Huazhu, et al., Beijing: Ordnance Industry Press, 2004). Common explosive ligands include $ClO_3^-$, $ClO_4^-$, $NO_3^-$, $ONC^-$, $N(NO_2)_2^-$, diazenyl, azide ions, and nitro ligands.

X of the present application is at least one anionic energetic ligand. In some embodiments, X is an oxidizing anionic energetic ligand. In some embodiments, X is a monovalent anionic energetic ligand. In some embodiments, X is a monovalent halogen-containing energetic ligand.

In some embodiments, the anionic energetic ligand (X) may be one, two or more of: $ClO_4^-$, $BrO_4^-$, $IO_4^-$, $ONC^-$, $NO_3^-$ and $N(NO_2)_2^-$.

In some embodiments, the anionic energetic ligand (X) may be one, two or more of: $ClO_4^-$, $BrO_4^-$ and $IO_4^-$.

A of the present application is at least one organic cation. In some embodiments, A is a reducing organic cation.

In some embodiments, A is at least one nitrogen-containing organic cation.

In some embodiments, A is at least one nitrogen-containing heterocycle organic cation.

In some embodiments, A is at least one nitrogen-containing six-membered heterocycle organic cation.

In some embodiments, A is one, two or more of organic cations formed by protonizing the following organic matters and derivatives of the organic cations: 1,4-diazabicyclo[2.2.2]octane, pyrazine, piperazine, 3-aminopyrrolidine, imidazoline, amino-triazole, amino-tetrazole, ethanediamine, cyanoguanidine, phenylenediamine, 1,5-diaminopentane, cyclohexanediamine and the like.

In some embodiments, A is selected from one, two or more of the following organic cation parents and derivatives thereof:

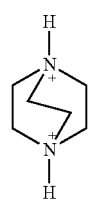

1,4-diazabicyclo[2.2.2]octane-1,4-diium,

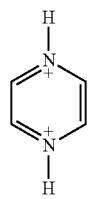

pyrazine-1,4-diium,

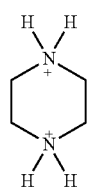

piperazine-1,4-diium,

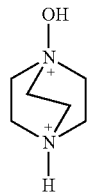

1-hydroxy-1,4-diazabicyclo[2.2.2]octane-1,4-diium,

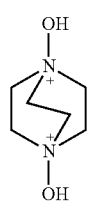

1,4-dihydroxy-1,4-diazabicyclo[2.2.2]octane-1,4-diium,

imidazolidine-1,3-diium,

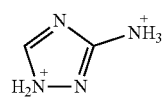

3-ammonio-1H-1,2,4-triazol-1-ium,

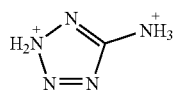

5-ammonio-2H-tetrazol-2-ium,

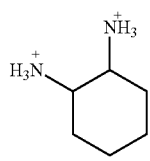

cyclohexane-1,2-diaminium,

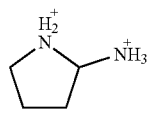

2-ammoniopyrrolidin-1-ium,

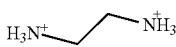

ethane-1,2-diaminium.

In some embodiments, A is selected from one, two or more of the following organic cation parents and derivatives thereof:

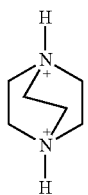

1,4-diazabicyclo[2.2.2]octane-1,4-diium,

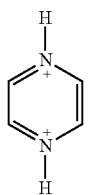

pyrazine-1,4-diium,

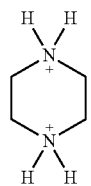

piperazine-1,4-diium,

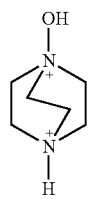

1-hydroxy-1,4-diazabicyclo[2.2.2]octane-1,4-diium,

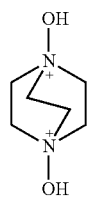

1,4-dihydroxy-1,4-diazabicyclo[2.2.2]octane-1,4-diium.

The derivatives of the organic cations of A are that hydrogen atoms bonded to the organic cation parents be substitute with substituent ligand(s) simultaneously or differently. Common substituent ligands include methyl, ethyl, isopropyl, tertiary butyl, hydroxy, oxo, carboxyl, halogen, sulfydryl, peroxyl, diazenyl, nitryl and the like. In some embodiments, the substituent ligand is selected from a group consisting of methyl, ethyl, isopropyl, tertiary butyl, hydroxy, oxo, carboxyl, halogen, sulfydryl, peroxyl, diazenyl, and nitryl. In some embodiments, the substituent is methyl.

In some embodiments, A is selected from a group consisting of

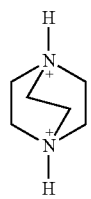

1,4-diazabicyclo[2.2.2]octane-1,4-diium,

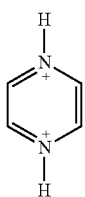

pyrazine-1,4-diium,

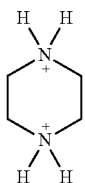

piperazine-1,4-diium,

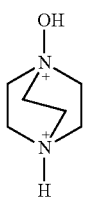

1-hydroxy-1,4-diazabicyclo[2.2.2]octane-1,4-diium,

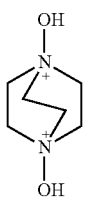

1,4-dihydroxy-1,4-diazabicyclo[2.2.2]octane-1,4-diium,
and the derivatives thereof;
wherein in said derivatives, at least one of the shown hydrogen atoms bonded to the organic cation parents is substituted with substituents selected from a group consisting of methyl, ethyl, isopropyl, tertiary butyl, hydroxy, oxo, carboxyl, halogen, sulfydryl, peroxyl, diazenyl, nitryl and the like. In some embodiments, the substituent ligand is selected from a group consisting of methyl, ethyl, isopropyl, tertiary butyl, hydroxy, oxo, carboxyl, halogen, sulfydryl, peroxyl, diazenyl, and nitryl.

In some embodiments, A is selected from a group consisting of
1,4-diazabicyclo[2.2.2]octane-1,4-diium, pyrazine-1,4-diium, piperazine-1,4-diium, 1-hydroxy-1,4-diazabicyclo[2.2.2]octane-1,4-diium, 1,4-dihydroxy-1,4-diazabicyclo[2.2.2]octane-1,4-diium, and the derivatives thereof; wherein in said derivatives, at least one of the hydrogen atoms bonded to the nitrogen atom of organic cation parents is substituted with substituents selected from a group consisting of methyl, ethyl, isopropyl, tertiary butyl, hydroxy, oxo, carboxyl, halogen, sulfydryl, peroxyl, diazenyl, nitryl and the like. In some embodiments, the substituent ligand is selected from a group consisting of methyl, ethyl, isopropyl, tertiary butyl, hydroxy, oxo, carboxyl, halogen, sulfydryl, peroxyl, diazenyl, and nitryl.

In some embodiments, A is selected from a group consisting of 1,4-diazabicyclo[2.2.2]octane-1,4-diium, pyrazine-1,4-diium, piperazine-1,4-diium, 1-hydroxy-1,4-diazabicyclo[2.2.2]octane-1,4-diium, 1,4-dihydroxy-1,4-diazabicyclo[2.2.2]octane-1,4-diium, and the derivatives thereof; wherein in the derivatives, at least one of the hydrogen atoms bonded to the nitrogen atom of the organic cation parents is substituted with substituents which is methyl.

In some embodiments, A is selected from a group consisting of 1,4-diazabicyclo[2.2.2]octane-1,4-diium, piperazine-1,4-diium, and the derivatives thereof, wherein in said derivatives, at least one of the hydrogen atoms bonded to the nitrogen atom of organic cation parents is substituted with at least one substituent, wherein each of the substituent is selected from a group consisting of hydroxyl and methyl.

In some embodiments, A is selected from a group consisting of 1,4-diazabicyclo[2.2.2]octane-1,4-diium, piperazine-1,4-diium, and the derivatives thereof, wherein in said derivatives, one of the hydrogen atoms bonded to the nitrogen atom of organic cation parents is substituted with methyl.

In some embodiments, A is selected from a group consisting of 1,4-diazabicyclo[2.2.2]octane-1,4-diium, piperazine-1,4-diium, 1-hydroxy-1,4-diazabicyclo[2.2.2]octane-1,4-diium, 1,4-dihydroxy-1,4-diazabicyclo[2.2.2]octane-1,4-diium, and the derivatives of 1,4-diazabicyclo[2.2.2]octane-1,4-diium, piperazine-1,4-diium; wherein in said derivatives, at least one of the hydrogen atoms bonded to the nitrogen atom of the organic cation parents is substituted with substituents which is methyl.

The B is at least one monovalent cation.

In some embodiments, B is selected from one, two or more of the following cations: an alkali metal ion, $NH_4^+$.

In some embodiments, the alkali metal ion is selected from one, two or more of $Na^+$, $K^+$, $Rb^+$ and $Cs^+$.

In some embodiments, A is selected from one, two or more of a 1,4-diazabicyclo[2.2.2]octane-1,4-diium, a 1-hydroxy-1,4-diazabicyclo[2.2.2]octane-1,4-diium, a 1,4-dihydroxy-1,4-diazabicyclo[2.2.2]octane-1,4-diium and derivatives thereof. In some embodiments, A is selected from one or two of organic cations such as the 1,4-diazabicyclo[2.2.2]octane-1,4-diium and the 1,4-dihydroxy-1,4-diazabicyclo[2.2.2]octane-1,4-diium.

In some embodiments, B is selected from one, two or more of $Na^+$, $K^+$ and $NH_4^+$. In some embodiments, B is selected from $Na^+$ and $NH_4^+$. In some embodiments, B is selected from $NH_4^+$.

In some embodiments, X is selected from one, two or more of $ClO_4^-$, $NO_3^-$ and $IO_4^-$. In some embodiments, X is selected from one or two of $ClO_4^-$ and $NO_3^-$, or selected from one or two of $ClO_4^-$ and $IO_4^-$. In some embodiments, X is selected from $ClO_4^-$.

In some embodiments, A is selected from one, two or more of organic cations such as a 1,4-diazabicyclo[2.2.2]octane-1,4-diium, a pyrazine-1,4-diiumpyrazine-1,4-diium, a piperazine-1.4-diiumpiperazine-1.4-diium, a 1-hydroxy-1,4-diazabicyclo[2.2.2]octane-1,4-diium and a 1,4-dihydroxy-1,4-diazabicyclo[2.2.2]octane-1,4-diium; B is selected from one, two or more of $Na^+$, $K^+$, $Rb^+$ and $NH_4^+$; and X is selected from one, two or more of $ClO_4^-$, $NO_3^-$ and $IO_4^-$; in some embodiments, X is selected from one or two of $ClO_4^-$ and $IO_4^-$, or selected from one or two of $ClO_4^-$ and $NO_3^-$.

In some embodiments, A is selected from one, two or more of organic cations such as a 1,4-diazabicyclo[2.2.2]octane-1,4-diium, a 1-hydroxy-1,4-diazabicyclo[2.2.2]octane-1,4-diium and a 1,4-dihydroxy-1,4-diazabicyclo[2.2.2]octane-1,4-diium; B is selected from one, two or more of $Na^+$, $K^+$, $Rb^+$ and $NH_4^+$; and X is selected from one or two of $ClO_4^-$ and $NO_3^-$, or one or two of $ClO_4^-$ and $IO_4^-$; in some embodiments, X is selected from $ClO_4^-$.

In some embodiments, A is selected from one or two of organic cations such as 1,4-diazabicyclo[2.2.2]octane-1,4-diium and 1,4-dihydroxy-1,4-diazabicyclo[2.2.2]octane-1,4-diium; B is selected from one, two or more of $Na^+$, $K^+$, $Rb^+$ and $NH_4^+$; and X is selected from one or two of $ClO_4^-$ and $NO_3^-$, or one or two of $ClO_4^-$ and $IO_4^-$; in some embodiments, X is selected from $ClO_4^-$.

In some embodiments, A is selected from one or two of organic cations such as a 1,4-diazabicyclo[2.2.2]octane-1,4-diium and a 1,4-dihydroxy-1,4-diazabicyclo[2.2.2]octane-1,4-diium; B is selected from one, two or more of $Na^+$, $K^+$ and $NH_4^+$; and X is selected from one or two of $ClO_4^-$ and $NO_3^-$, or one or two of $ClO_4^-$ and $IO_4^-$; in some embodiments, X is selected from $ClO_4^-$.

In some embodiments, A is an organic cation such as a 1,4-diazabicyclo[2.2.2]octane-1,4-diium; B is selected from one or two of $Na^+$ and $NH_4^+$; and X is selected from one or two of $ClO_4^-$ and $NO_3^-$, or one or two of $ClO_4^-$ and $IO_4^-$; in some embodiments, X is selected from $ClO_4^-$.

In some embodiments, A and X are selected from the above-mentioned any possible selections, and B is selected from $NH_4^+$.

In some embodiments, A is selected from one, two or more of organic cations such as a 1,4-diazabicyclo[2.2.2]octane-1,4-diium, a pyrazine-1,4-diium, a piperazine-1,4-diium, a 1-hydroxy-1,4-diazabicyclo[2.2.2]octane-1,4-diium, a 1,4-dihydroxy-1,4-diazabicyclo[2.2.2]octane-1,4-diium and derivatives thereof, X is selected from one, two or more of $ClO_4^-$, $BrO_4^-$ and $IO_4^-$; and B is selected from $NH_4^+$.

When B is $NH_4^+$, and after the compound completely explodes, no metallic salt solid substances remain, and gas generated per mole may be up to 15.25 moles. With this nature, the compound is more favorably used as an explosive, rocket fuel, a propellant, and a gas generants of safety air bags, etc., and is particularly suitable for application fields with high requirements for the gas yield. For example, the compound is used as the rocket fuel.

In some embodiments, A and X are selected from the above-mentioned any possible selections, and B is $Na^+$.

In some embodiments, A is selected from one, two or more of organic cations such as a 1,4-diazabicyclo[2.2.2]octane-1,4-diium, a pyrazine-1,4-diium, a piperazine-1,4-diium, a 1-hydroxy-1,4-diazabicyclo[2.2.2]octane-1,4-diium, a 1,4-dihydroxy-1,4-diazabicyclo[2.2.2]octane-1,4-diium and derivatives thereof; X is selected from one, two or more of $ClO_4^-$, $BrO_4^-$ and $IO_4^-$; and B is selected from $Na^+$.

In some embodiments, A is 1,4-diazabicyclo[2.2.2]octane-1,4-diium, X is $ClO_4^-$, and B is $Na^+$.

When B is $Na^+$, particular advantages are as follows: theoretically, in comparison with such a situation that B is $K^+$, the density is reduced. It is generally considered that the reduced density ρ may reduce the performance of the energetic material (a Kamlet-Jacob equation of deducing a detonation velocity D and a detonation pressure P of the energetic material: $D=1.01\Phi^{1/2}(1+1.30\rho)$, $P=1.558\Phi\rho^2$, where $\Phi=31.68N(MQ)^{1/2}$; N is a gas mole number generated by unit mass of the material; M is an average mole mass of a gas product; and Q is a heat output per unit mass of the material. Therefore, the density is in positive correlation with the influence of the detonation velocity and the detonation pressure, and is particularly in square index relation with the influence of the detonation pressure). However, the present application finds that (see Embodiment 1) when the compound is used as the energetic material, it has been simply and clearly foreseen that lightweight sodium ions may reduce the density of the material, according to which, speculation can be made that negative effects may be generated on the detonation velocity and the detonation pressure of the material, but all experiments and theoretical calculation have proven that the use of the sodium ions achieves a better effect on multiple performances instead. For example, through comparison of DAP-1 (see Embodiment 1, B of the perovskite type compound is $Na^+$) and DAP-2 (see Embodiment 2, B of the perovskite type compound is $K^+$), the heat output per unit mass is increased, and the gas mole number per unit mass is increased, so that theoretical forecasted values of the detonation velocity and the detonation pressure of DAP-1 are both higher than those of DAP-2. In addition, sodium perchlorate serving as a raw material of DAP-1 is easier to dissolve in a polar solvent than potassium perchlorate serving as a raw material of DAP-2, so that the amount of a solvent for synthesizing DAP-1 is much less than the amount of a solvent for synthesizing DAP-2. Therefore, in experiment and manufacturing, DAP-1 is more convenient to synthesize. DAP-1 is possibly more suitable to be applied to the fields of high explosives and propellants than DAP-2.

In some embodiments, A and X are selected from the above-mentioned any possible selections, and X is $NO_3^-$.

In some embodiments, A is selected from one, two or more of organic cations such as a 1,4-diazabicyclo[2.2.2]octane-1,4-diium, a pyrazine-1,4-diium, a piperazine-1,4-diium, a 1-hydroxy-1,4-diazabicyclo[2.2.2]octane-1,4-diium, a 1,4-dihydroxy-1,4-diazabicyclo[2.2.2]octane-1,4-diium and derivatives thereof; B is selected from one, two or more of $Na^+$, $K^+$, $Rb^+$ and $NH_4^+$; and X is $NO_3^-$.

When X is $NO_3^-$, the compound does not contain a halogen element, so that no hydrogen halide gas is produced after the explosion of the compound, thereby reducing characteristic signals and relieving environmental pollution. This nature enables the compound to be particularly suitable for application fields with requirements for low characteristic signals. For example, the compound is used as a low characteristic signal propellant or rocket fuel.

$ABX_3$ may be obtained by the reaction among the A component, the B component and the X component which are added into a liquid reaction system in any order. In some embodiments, the liquid reaction system is a polar solvent capable of dissolving the A component, the B component and the X component, or is obtained by using a known synthesis method. There is no limitation on reaction temperature, which may be adjusted within an extremely large range, such as 0 to 100° C.

In some embodiments, the present application provides a preparation method of the compound, including:
1) adding an A component into a polar solvent, then adding an X component, and uniformly stirring;
2) dissolving a B component into the polar solvent;
3) mixing a solution obtained in step 1) with a solution obtained in step 2), performing full stirring and filtration, washing residues with ethanol, and performing vacuum drying, thus obtaining a white powdery energetic compound.

In some embodiments, the said A component is at least one of 1,4-diazabicyclo[2.2.2]octane or a derivative thereof, pyrazine or a derivative thereof, piperazine or a derivative thereof, 1,4-diazabicyclo[2.2.2]octane 1-oxide or a derivative thereof, 1,4-diazabicyclo[2.2.2]octane 1,4-dioxide or a derivative thereof, organic salt containing a 1,4-diazabicyclo[2.2.2]octane-1,4-diium or a derivative thereof, organic salt containing a pyrazine-1,4-diium or a derivative thereof, organic salt containing a piperazine-1,4-diium or a derivative thereof, organic salt containing a 1-hydroxy-1,4-diazabicyclo[2.2.2]octane-1,4-diium or a derivative thereof, and organic salt containing a 1,4-dihydroxy-1,4-diazabicyclo[2.2.2]octane-1,4-diium or a derivative thereof.

In some embodiments, the said A component is at least one of 1,4-diazabicyclo[2.2.2]octane or a derivative thereof, pyrazine or a derivative thereof, piperazine or a derivative thereof, 1,4-diazabicyclo[2.2.2]octane 1-oxide or a derivative thereof, 1,4-diazabicyclo[2.2.2]octane 1,4-dioxide or a derivative thereof, salt or solution containing a 1,4-diazabicyclo[2.2.2]octane-1,4-diium or a derivative thereof, salt or solution containing a pyrazine-1,4-diium or a derivative thereof, salt or solution containing a piperazine-1,4-diium or a derivative thereof, salt or solution containing a 1-hydroxy-1,4-diazabicyclo[2.2.2]octane-1,4-diium or a derivative thereof, and salt or solution containing a 1,4-dihydroxy-1,4-diazabicyclo[2.2.2]octane-1,4-diium or a derivative thereof, wherein in said derivatives, at least one of the hydrogen atoms bonded to the organic cation parents is substituted with substituents selected from a group consisting of methyl, ethyl, isopropyl, tertiary butyl, hydroxy, oxo, carboxyl, halogen, sulfydryl, peroxyl, diazenyl, nitryl and the like. In some embodiments, the substituent ligand is selected from a group consisting of methyl, ethyl, isopropyl, tertiary butyl, hydroxy, oxo, carboxyl, halogen, sulfydryl, peroxyl, diazenyl, and nitryl.

In some embodiments, the said A component is at least one of 1,4-diazabicyclo[2.2.2]octane or a derivative thereof, pyrazine or a derivative thereof, piperazine or a derivative thereof, 1,4-diazabicyclo[2.2.2]octane 1-oxide or a derivative thereof, 1,4-diazabicyclo[2.2.2]octane 1,4-dioxide or a derivative thereof, salt or solution containing a 1,4-diazabicyclo[2.2.2]octane-1,4-diium or a derivative thereof, salt or solution containing a pyrazine-1,4-diium or a derivative thereof, salt or solution containing a piperazine-1,4-diium or a derivative thereof, salt or solution containing a 1-hydroxy-1,4-diazabicyclo[2.2.2]octane-1,4-diium or a derivative thereof, and salt or solution containing a 1,4-dihydroxy-1,4-diazabicyclo[2.2.2]octane-1,4-diium or a derivative thereof, wherein in said derivatives, at least one of the hydrogen atoms bonded to the nitrogen atom of organic cation parents is substituted with substituents selected from a group consisting of methyl, ethyl, isopropyl, tertiary butyl, hydroxy, oxo, carboxyl, halogen, sulfydryl, peroxyl, diazenyl, nitryl and the like.

In some embodiments, the said A component is at least one of 1,4-diazabicyclo[2.2.2]octane or a derivative thereof, pyrazine or a derivative thereof, piperazine or a derivative thereof, 1,4-diazabicyclo[2.2.2]octane 1-oxide or a derivative thereof, 1,4-diazabicyclo[2.2.2]octane 1,4-dioxide or a derivative thereof, salt or solution containing a 1,4-diazabicyclo[2.2.2]octane-1,4-diium or a derivative thereof, salt or solution containing a pyrazine-1,4-diium or a derivative thereof, salt or solution containing a piperazine-1,4-diium or a derivative thereof, salt or solution containing a 1-hydroxy-1,4-diazabicyclo[2.2.2]octane-1,4-diium or a derivative thereof, and salt or solution containing a 1,4-dihydroxy-1,4-diazabicyclo[2.2.2]octane-1,4-diium or a derivative thereof, wherein in said derivatives, at least one of the hydrogen atoms bonded to the nitrogen atom of organic cation parents is substituted with methyl.

In some embodiments, the said A component is at least one of 1,4-diazabicyclo[2.2.2]octane or a derivative thereof, piperazine or a derivative thereof, salt or solution containing a 1,4-diazabicyclo[2.2.2]octane-1,4-diium or a derivative thereof, and salt or solution containing a piperazine-1,4-diium or a derivative thereof, wherein in said derivatives, at least one of the hydrogen atoms bonded to the nitrogen atom of organic cation parents is substituted with methyl.

In some embodiments, the said A component is at least one of 1,4-diazabicyclo[2.2.2]octane or a derivative thereof, piperazine or a derivative thereof, salt or solution containing a 1,4-diazabicyclo[2.2.2]octane-1,4-diium or a derivative thereof, and salt or solution containing a piperazine-1,4-diium or a derivative thereof, wherein in said derivatives, at least one of the hydrogen atoms bonded to the nitrogen atom of organic cation parents is substituted with methyl, hydroxyl or oxo ligand.

In some embodiments, the said A component is at least one of 1,4-diazabicyclo[2.2.2]octane or a derivative thereof, piperazine or a derivative thereof, 1,4-diazabicyclo[2.2.2]octane 1-oxide, 1,4-diazabicyclo[2.2.2]octane 1,4-dioxide, salt or solution containing a 1,4-diazabicyclo[2.2.2]octane-1,4-diium or a derivative thereof, salt or solution containing a piperazine-1,4-diium or a derivative thereof, salt or solution containing a 1-hydroxy-1,4-diazabicyclo[2.2.2]octane-1,4-diium, and salt or solution containing a 1,4-dihydroxy-1,4-diazabicyclo[2.2.2]octane-1,4-diium, wherein in said derivatives, at least one of the hydrogen atoms bonded to the nitrogen atom of organic cation parents is substituted with methyl.

In some embodiments, the said A component is at least one of: 1,4-diazabicyclo[2.2.2]octane, pyrazine, piperazine, 1,4-diazabicyclo[2.2.2]octane 1-oxide, 1,4-diazabicyclo[2.2.2]octane 1,4-dioxide, or a derivative thereof, wherein in said derivatives, at least one of the hydrogen atoms bonded to the nitrogen atom of organic cation parents is substituted with methyl.

In some embodiments, the said A component is at least one of salt or solution containing: a 1,4-diazabicyclo[2.2.2]octane-1,4-diium, pyrazine-1,4-diium, piperazine-1,4-diium, 1-hydroxy-1,4-diazabicyclo[2.2.2]octane-1,4-diium, 1,4-dihydroxy-1,4-diazabicyclo[2.2.2]octane-1,4-diium, or a derivative thereof, wherein in said derivatives, at least one of the hydrogen atoms bonded to the nitrogen atom of organic cation parents is substituted with methyl, wherein said salt or solution containing chloride or iodide.

In some embodiments, the said A component is at least one of, chloride or iodide of, a 1,4-diazabicyclo[2.2.2]octane-1,4-diium, pyrazine-1,4-diium, piperazine-1,4-diium, 1-hydroxy-1,4-diazabicyclo[2.2.2]octane-1,4-diium, 1,4-dihydroxy-1,4-diazabicyclo[2.2.2]octane-1,4-diium, or a derivative thereof, wherein in said derivatives, at least one of the hydrogen atoms bonded to the nitrogen atom of organic cation parents is substituted with methyl.

In some embodiments, a cation of the B component is selected from one, two or more of alkali metal ions and $NH_4^+$. The B component is at least one of ammonium salt, sodium salt, potassium salt, rubidium salt, cesium salt, ammonium alkali, sodium alkali, potassium alkali, rubidium alkali and cesium alkali.

In some embodiments, said X component is at least one of a halogen-containing energetic acids and halogen-containing energetic salts.

In some embodiments, said polar solvent is one, two or more of water, ethanol and methanol.

In some embodiments, the organic salt containing the 1,4-diazabicyclo[2.2.2]octane-1,4-diium is hydrochloride of 1,4-diazabicyclo[2.2.2]octane.

In some embodiments, the said organic salt containing the 1,4-diazabicyclo[2.2.2]octane-1,4-diium derivative is at least one of hydrochloride of 2-hydroxy-1,4-diazabicyclo[2.2.2]octane, hydrochloride of 2-carbonyl-1,4-diazabicyclo[2.2.2]octane and hydrochloride of 2-methyl-1,4-diazabicyclo[2.2.2]octane.

In some embodiments, the said organic salt containing the pyrazine-1,4-diium is hydrochloride of pyrazine.

In some embodiments, the said organic salt containing the pyrazine-1,4-diium derivative is at least one of hydrochloride of 2-hydroxy-pyrazine and hydrochloride of 2-methyl-pyrazine.

In some embodiments, the said organic salt containing the piperazine-1,4-diium is hydrochloride of piperazine.

In some embodiments, the said organic salt containing the piperazine-1,4-diium derivative is at least one of hydrochloride of 2-hydroxy-piperazine and hydrochloride of 2-methyl-piperazine.

In some embodiments, the said organic salt containing the 1-hydroxy-1,4-diazabicyclo[2.2.2]octane-1,4-diium is hydrochloride of 1,4-diazabicyclo[2.2.2]octane 1-oxide.

In some embodiments, the said organic salt containing the 1-hydroxy-1,4-diazabicyclo[2.2.2]octane-1,4-diium derivative is at least one of hydrochloride of 2-hydroxy-1,4-diazabicyclo[2.2.2]octane 1-oxide and hydrochloride of 2-carbonyl-1,4-diazabicyclo[2.2.2]octane 1-oxide.

In some embodiments, the said organic salt containing the 1,4-dihydroxy-1,4-diazabicyclo[2.2.2]octane-1,4-diium is hydrochloride of 1,4-diazabicyclo[2.2.2]octane 1,4-dioxide.

In some embodiments, the said organic salt containing the 1,4-dihydroxy-1,4-diazabicyclo[2.2.2]octane-1,4-diium derivative is at least one of 2-hydroxy-1,4-diazabicyclo[2.2.2]octane 1,4-dioxide and hydrochloride of 2-carbonyl-1,4-diazabicyclo[2.2.2]octane 1,4-dioxide.

In some embodiments, the said ammonium salt is at least one of ammonium perchlorate, ammonium tetrafluoroborate, ammonium periodate, ammonium perrhenate, ammonium carbonate, ammonium nitrate, ammonium phosphate, ammonium chloride and ammonium fluoride.

In some embodiments, the said sodium salt is at least one of sodium perchlorate, sodium tetrafluoroborate, sodium periodate, sodium perrhenate, sodium carbonate, sodium nitrate, sodium phosphate, sodium chloride and sodium fluoride.

In some embodiments, the said potassium salt is at least one of potassium perchlorate, potassium tetrafluoroborate, potassium periodate, potassium perrhenate, potassium carbonate, potassium nitrate, potassium phosphate, potassium chloride and potassium fluoride.

In some embodiments, the said rubidium salt is at least one of rubidium perchlorate, rubidium tetrafluoroborate, rubidium periodate, rubidium perrhenate, rubidium carbonate, rubidium nitrate, rubidium phosphate, rubidium chloride and rubidium fluoride.

In some embodiments, the said cesium salt is at least one of cesium perchlorate, cesium tetrafluoroborate, cesium periodate, cesium perrhenate, cesium carbonate, cesium nitrate, cesium phosphate, cesium chloride and cesium fluoride.

In some embodiments, the said ammonium alkali is ammonia water.

In some embodiments, the said sodium alkali is sodium hydroxide.

In some embodiments, the said potassium alkali is potassium hydroxide.

In some embodiments, the said rubidium alkali is rubidium hydroxide.

In some embodiments, the said cesium alkali is cesium hydroxide.

In some embodiments, said X component is a perchlorate radical containing substance. For example, said X component is a perchloric acid.

In some embodiments, the said polar solvent is at least one of water, ethanol and methanol.

In some embodiments, when the perovskite type compound $ABX_3$ contains a perchlorate radical, characteristic peaks of an infrared absorption spectrum of the perchlorate radical are ranged from 1070 to 1100 $cm^{-1}$ and 617 to 637 $cm^{-1}$.

When the perovskite type compound $ABX_3$ contains a nitrate radical, characteristic peaks of an infrared absorption spectrum of the nitrate radical are ranged from 1375 to 1390 $cm^{-1}$ and 845 to 860 $cm^{-1}$.

When in a cubic system, the $2\theta$ angle locating the characteristic peaks of a powder X-ray diffraction pattern is about: $12.1\pm0.70°$, $21.1\pm1.00°$ and $24.4\pm1.20°$. Further, the $2\theta$ angle locating the characteristic peaks of a powder X-ray diffraction pattern is about: $12.1\pm0.70°$, $21.1\pm1.00°$, $24.4\pm1.20°$, $27.4\pm1.30°$ and $36.57\pm0.88°$.

Or, in a monoclinic system, an $2\theta$ angle locating the characteristic peaks of a powder X-ray diffraction pattern is about: $12.6\pm0.5°$, $21.7\pm0.5°$, $22.4\pm0.5°$, $22.7\pm0.5°$, $25.4\pm0.5°$ and $26.8\pm0.5°$. Further, the $2\theta$ angle locating the characteristic peaks of a powder X-ray diffraction pattern is about: $12.6\pm0.5°$, $21.7\pm0.5°$, $22.4\pm0.5°$, $22.7\pm0.5°$, $25.4\pm0.5°$, $26.8\pm0.5°$, $27.2\pm0.5°$, $37.7\pm0.5°$ and $38.4\pm0.5°$.

Or, in a hexagonal system, an $2\theta$ angle locating the characteristic peaks of a powder X-ray diffraction pattern is about: $17.7\pm0.5°$, $20.4\pm0.5°$, $23.9\pm0.5°$, $24.8\pm0.5°$, $29.7\pm0.5°$ and $30.5\pm0.5°$. Further, the $2\theta$ angle locating the characteristic peaks of a powder X-ray diffraction pattern is about: $10.3\pm0.5°$, $17.7\pm0.5°$, $20.4\pm0.5°$, $23.9\pm0.5°$, $24.8\pm0.5°$, $27.0\pm0.5°$, $29.7\pm0.5°$, $30.5\pm0.5°$ and $32.2\pm0.5°$ and $37.0\pm0.5°$.

The present application has the outstanding beneficial effects that:
(1) the energetic compound of the present application has high detonation heat and a high energy density; the theoretical detonation heat may be up to 1.53 kcal/g; a crystal density is within a range of 1.8 to 2.3 $g/cm^3$; the corresponding energy density may be up to 3.11 kcal/$cm^3$;
(2) the energetic compound of the present application has a high detonation velocity; the theoretical detonation velocity may be up to 8.85 km/s calculated according to the Kamlet-Jacob formula;
(3) the energetic compound of the present application has a high detonation pressure; the theoretical detonation pressure may be up to 37.3 GPa calculated according to the Kamlet-Jacob formula;
(4) the energetic compound of the present application has high safety, as well as extremely low impact, friction and electrostatic sensitivities, and the thermo-activated burst point temperature may be 340° C.;
(5) the energetic compound of the present application is nonvolatile, and may be stored for a long time without decomposition or hygroscopic characteristic;
(6) the energetic compound of the present application has single crystallinity at room temperature, and can be safely prepared in batches from cheap and readily-available raw materials through a simple process.

DETAILED DESCRIPTION OF THE INVENTION

Figure 1:
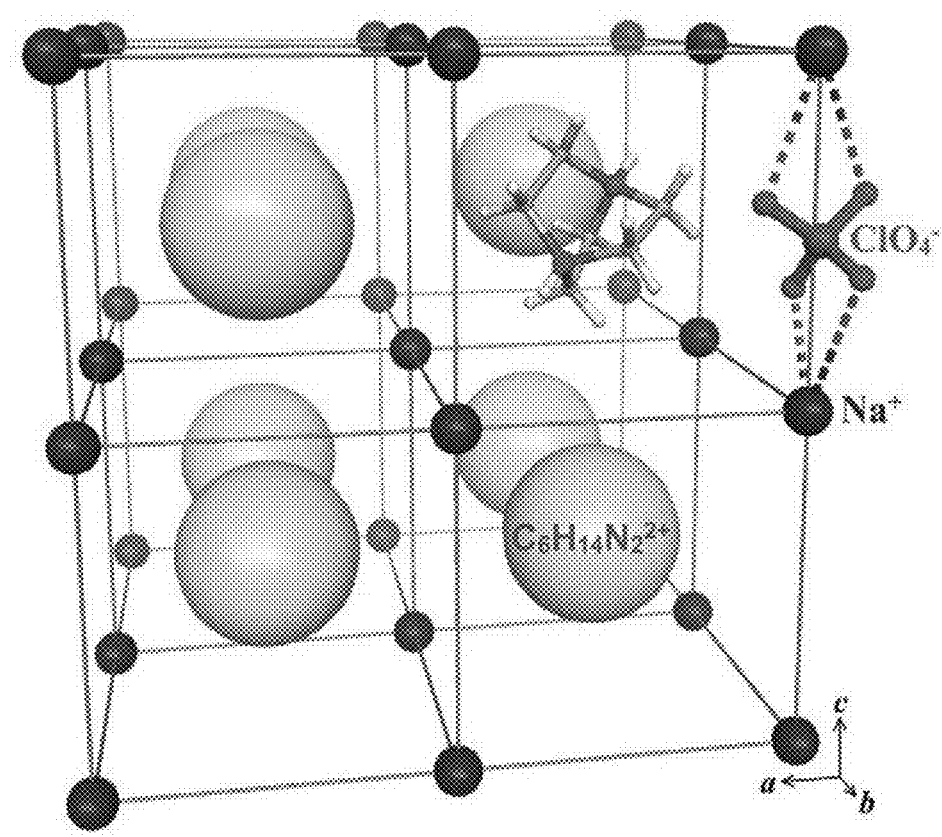
FIG. 1 is a structural schematic diagram of energetic compound DAP-1.

The inventor designs a series of perovskite type compounds having energetic groups, and makes relevant experiments and researches on the prospect of these compounds serving as novel high-performance explosives in the energetic field. In the present application, such perovskite type energetic compounds ($ABX_3$, corresponding to an abbreviation DAP in the following embodiments and endowed with respective numbers) having the energetic ligands are provided. Experiments and calculations indicate that their energy densities and explosive performance may be comparable with those of high-performance active-duty military explosives RDX and HMX. Furthermore, the compounds have excellent safety performance, with non-volatile and non-hygroscopic characteristics, and are prepared from cheap and readily-available raw materials through a simple synthesis process. These compounds are novel energetic compounds having practical values in the energetic fields.

The $ABX_3$ may be synthesized by a synthesis method of the present application. A synthesis method (Z. M. Jin, Y. J. Pan, X. F. Li, M. L. Hu, L. Shen, *Journal of Molecular Structure*, 2003, 660, 67) of a perovskite type compound $(C_6H_{14}N_2)[K(ClO_4)_3]$, which is disclosed by Z. M. Jin et al, may be also employed for reference.

X in $ABX_3$ is at least one anionic energetic ligand. The energetic ligand is an explosive ligand. Common explosive ligands include, but not limited to, $ClO_3^-$, $ClO_4^-$, $IO_4^-$, $NO_3^-$, $ONC^-$, diazenyl, azide ion, nitryl, and the like.

In $ABX_3$, for example, X may include one or more ions. For example, 2, 3, 4, 5, 6, 7, 8, 9, 10 . . . types of X ions may exist at the same time. The same is true for A and B. When perovskite includes more than one type of A cations, different A cations may be distributed at A sites in an ordered or disordered manner. When the perovskite includes more than one type of B cation, different B cations may be distributed at B sites in an ordered or disordered manner. When the perovskite includes more than one type of X anion, different X anions may be distributed at X sites in an ordered or disordered manner.

Based on this nature, the above-mentioned "X is at least one . . . ligand/ion", "A is at least one . . . ligand/ion", "B is at least one . . . ligand/ion", "X is selected from . . . ", "A is selected from . . . ", "B is selected from . . . ", etc. should be understood for example that for X, an $ABX_3$ three-dimensional framework includes many X sites, each of which consists of one type of ions. In the three-dimensional framework, the multiple X sites may consist of the same type of ions, and also may consist of different types of ions. When the X sites consist of different ions, at least some sites (or most sites) are . . . ligands/ions. At this moment, such a situation that a few of sites in the whole $ABX_3$ three-dimensional framework are not the . . . ligands/ions or some other foreign ions is not excluded as long as the number of these sites may not affect the overall performance to a large extent. The few of sites may, for example, have the mole number less than 50 percent, for example, not more than 40 percent, 30 percent, 25 percent, 20 percent, 15 percent, 10 percent, 9 percent, 8 percent, 7 percent, 6 percent, 5 percent, 4 percent, 3 percent, 2 percent or 1 percent . . . . For A and B, it is the same.

The present application performs various identification and characterization methods including powder X-ray diffraction identification, single-crystal structure characterization test, infrared spectral characterization, thermal stability characterization, differential scanning calorimetry (DSC), sensitivity characterization, and detonation heat/detonation pressure/detonation velocity calculation.

There into, powder X-ray diffraction data under a room temperature condition are collected on a Bruker D8 Advance diffractometer by adopting a Cu-Kα ray. A scanning mode is as follows: θ: 2θ linkage, stepping scanning, a 2θ step length being 0.02°. Single crystal X-ray diffraction data are collected on an Oxford Gemini S Ultra CCD diffractometer through a graphite monochromator in a ω scanning manner by using a Mo-Kα X-ray. An SADABS program is adopted for absorption correction. A direct method is used for analysis, and then all non-hydrogen coordinates are calculated by using a differential Fourier function method and a least square method, and finally the structure is refined by using a full-matrix least-square technique. Organic hydrogen atoms are generated geometrically. The calculation work is completed on a PC by using Olex$^2$ and SHELX program packages. Infrared spectral data are acquired on an IR Tensor 27 instrument. A dried sample and KBr are pressed into a transparent thin-sheet test sample. Thermogravimetric analysis is collected on a TA Q50 instrument in a nitrogen atmosphere at a scanning speed of 5° C./min. A DSC curve is collected on a TA DSC Q2000 instrument in the nitrogen atmosphere at the scanning speed of 5° C./min.

The sensitivity characterization is to test impact, friction and thermal sensitivities according to the National Military Standards GJB772A-97 of the People's Republic of China. The impact sensitivity is tested by a 601.1 explosive probability method. The friction sensitivity is tested by a 602.1 explosive probability method. The thermal sensitivity is tested by a 606.1-burst point 5 s delay method. The electrostatic sensitivity is tested by the third section of the industrial initiating explosive material test method WJ/T 9038.3-2004: electrostatic-spark sensitivity test.

At a room temperature, characteristic peaks of a perchlorate radical ligand in an infrared absorption spectrum are ranged from 1070 to 1100 cm$^{-1}$ (corresponding to asymmetric stretching vibration) and 617 to 637 cm$^{-1}$ (corresponding to asymmetric bending vibration). Characteristic peaks of a nitrate radical ligand in the infrared absorption spectrum are ranged from 1375 to 1390 cm$^{-1}$ (corresponding to asymmetric stretching vibration) and 845 to 860 cm$^{-1}$ (corresponding to asymmetric bending vibration).

In one embodiment, an adopted compound serving as an energetic material is $(C_6H_{14}N_2)[Na(ClO_4)_3]$ (which is recorded as DAP-1), and is crystallized in the cubic space group Pa-3 at 223 K, with a cell length of 14.1537(1)Å. An 2θ angle locating the characteristic peaks of a powder X-ray diffraction pattern (Cu-Kα X-ray) of the compound at the room temperature is about: 12.3±0.5°, 21.5±0.5°, 24.9±0.5°, 27.9±0.5°, 35.6±0.5° and 37.2±0.5°. Athermal stability analysis result shows that an explosion temperature of the compound may be up to 360° C. A differential scanning calorimetry result shows that heat released at 360° C. is 4398 J/g. A safety characterization result shows that DAP-1 is insensitive in impact sensitivity, friction sensitivity and electrostatic-spark sensitivity tests under the National Military Standards. Under the standard of Federal Institute for Material Research and Testing (BAM), the impact sensitivity of DAP-1 is about 17 J, and the friction sensitivity is about 36 N. The burst point of DAP-1 is 340° C. (5 s delay method). Detonation heat, detonation velocity and detonation pressure values obtained according to a Density Functional Theory (DFT) are respectively 1.53 kcal/g, 8.85 km/s and 37.31 GPa.

In another embodiment, an adopted compound serving as the energetic material is $(C_6H_{14}N_2)[K(ClO_4)_3]$ (which is recorded as DAP-2), and is crystallized in the cubic space group Pa-3 at 223 K, with a cell length of 14.2910(1)Å. An 2θ angle locating the characteristic peaks of a powder X-ray diffraction pattern (Cu-Kα X-ray) of the compound at the room temperature is about: 12.15±0.5°, 21.27±0.5°, 24.63±0.5°, 27.64±0.5°, 35.20±0.5° and 36.89±0.5°. Athermal stability analysis result shows that the explosion temperature of the compound may be 362° C. A differential scanning calorimetry result shows that heat released at 377° C. is 4076 J/g. A safety characterization result shows that under the standard of Federal Institute for Material Research and Testing (BAM), the impact sensitivity of DAP-2 is about 16 J, and the friction sensitivity is about 42 N. Detonation heat, detonation velocity and detonation pressure values obtained theoretically by the DFT are respectively 1.46 kcal/g, 8.64 km/s and 35.73 GPa.

In another embodiment, an adopted compound serving as the energetic material is $(C_6H_{14}N_2)[Rb(ClO_4)_3]$ (which is recorded as DAP-3), and is crystallized in the cubic space group Pa-3 at 223 K, with a cell length of 14.453(2)Å. An 2θ angle locating the characteristic peaks of a powder X-ray diffraction pattern (Cu-Kα X-ray) of the compound at the room temperature is about: 12.0±0.5°, 21.0±0.5°, 24.3±0.5°, 27.3±0.5°, 34.7±0.5° and 36.4±0.5°. A thermal stability analysis result shows that the explosion temperature of the compound may be up to 343° C. A differential scanning calorimetry result shows that heat released at 369° C. is 3797 J/g. A safety characterization result shows that under the standard of the Federal Institute for Material Research and Testing (BAM), the impact sensitivity of DAP-3 is about 22 J, and the friction sensitivity is about 28 N. Detonation heat, detonation velocity and detonation pressure values obtained theoretically by the DFT are respectively 1.33 kcal/g, 8.43 km/s and 35.14 GPa.

In another embodiment, an adopted compound serving as the energetic material is $(C_6H_{14}N_2)[NH_4(ClO_4)_3]$ (which is recorded as DAP-4), and is crystallized in the cubic space group Pa-3 at 223 K, with a cell length of 14.4264(1)Å. An 2θ angle locating the characteristic peaks of a powder X-ray diffraction pattern (Cu-Kα X-ray) diffraction of the compound at the room temperature is about: 12.0±0.5°, 21.0±0.5°, 24.4±0.5°, 27.3±0.5°, 34.8±0.5° and 36.5±0.5°. A thermal stability analysis result shows that the explosion temperature of the compound may be up to 370° C. A differential scanning calorimetry result shows that heat released at 364° C. is 5177 J/g. A safety characterization result shows that under the standard of Federal Institute for Material Research and Testing (BAM), the impact sensitivity of DAP-4 is about 23 J, and the friction sensitivity is about 36 N.

In another embodiment, an adopted compound serving as the energetic material is $(C_6H_{14}N_2O_2)[K(ClO_4)_3]$ (which is recorded as DAP-O22), and is crystallized in the cubic space group Fm-3c at 298 K, with a cell length of 14.745(3)Å. An 2θ angle locating the characteristic peaks of a powder X-ray diffraction pattern (Cu-Kα X-ray) of the compound at the room temperature is about: 11.9±0.5°, 20.8±0.5°, 24.1±0.5°, 27.0±0.5°, 34.4±0.5° and 36.1±0.5°. A thermal stability analysis result shows that a detonation temperature of the compound may be 354° C. A differential scanning calorimetry result shows that heat released at 358° C. is 5424 J/g. A safety characterization result shows that under the standard of the Federal Institute for Material Research and Testing (BAM), the impact sensitivity of DAP-O22 is about 11 J, and the friction sensitivity is about 14 N.

In another embodiment, an adopted compound serving as the energetic material is $(C_6H_{14}N_2O)[K(ClO_4)_3]$ (which is recorded as DAP-O12). An 2θ angle locating the characteristic peaks of a powder X-ray diffraction pattern (Cu-Kα X-ray) of the compound at the room temperature is about: 12.1±0.5°, 21.1±0.5°, 24.4±0.5°, 27.3±0.5°, 34.8±0.5° and 36.5±0.5°.

In another embodiment, an adopted compound serving as the energetic material is $(C_6H_{14}N_2O_2)[NH_4(ClO_4)_3]$ (which is recorded as DAP-O24). An 2θ angle locating the characteristic peaks of a powder X-ray diffraction pattern (Cu-Kα X-ray) of the compound at the room temperature is about: 11.9±0.5°, 20.8±0.5°, 24.0±0.5°, 27.0±0.5°, 34.4±0.5° and 36.0±0.5°. A differential scanning calorimetry result shows that heat released at 357° C. is 4632 J/g. A safety characterization result shows that under the standard of the Federal Institute for Material Research and Testing (BAM), the impact sensitivity of DAP-O24 is about 4 J, and the friction sensitivity is about 32 N.

In another embodiment, an adopted compound serving as the energetic material is $(C_4H_{12}N_2)[Na(ClO_4)_3]$ (which is recorded as PAP-1). An 2θ angle locating the characteristic peaks of a powder X-ray diffraction pattern (Cu-Kα X-ray) of the compound at the room temperature is about: 12.6±0.5°, 21.7±0.5°, 22.4±0.5°, 22.7±0.5°, 25.4±0.5°, 26.8±0.5°, 27.2±0.5°, 37.7±0.5° and 38.4±0.5°. A differential scanning calorimetry result shows that heat released at 375° C. is 4685 J/g.

In another embodiment, an adopted compound serving as the energetic material is $(C_4H_{12}N_2)[NH_4(ClO_4)_3]$ (which is recorded as PAP-4). A differential scanning calorimetry result shows that heat released at 356° C. is 3780 J/g.

In another embodiment, an adopted compound serving as the energetic material is $(C_6H_{14}N_2)[K(NO_3)_3]$ (which is recorded as DAN-2). An 2θ angle locating the characteristic peaks of a powder X-ray diffraction pattern (Cu-Kα X-ray) of the compound at the room temperature is about: 12.6±0.5°, 17.9±0.5°, 22.0±0.5°, 25.5±0.5°, 28.6±0.5°, 31.3±0.5°, 36.4±0.5°, 38.7±0.5°, 40.9±0.5° and 43.0±0.5°. A differential scanning calorimetry result shows that heat released at 177° C. is 1222 J/g. A safety characterization result shows that under the standard of the Federal Institute for Material Research and Testing (BAM), the impact sensitivity of DAN-2 is about 29 J, and the friction sensitivity is more than 360 N.

In another embodiment, an adopted compound serving as the energetic material is $(C_6H_{14}N_2)[NH_4(NO_3)_3]$ (which is recorded as DAN-4). An 2θ angle locating the characteristic peaks of a powder X-ray diffraction pattern (Cu-Kα X-ray) of the compound at the room temperature is about: 10.3±0.5°, 17.7±0.5°, 20.4±0.5°, 23.9±0.5°, 24.8±0.5°, 27.0±0.5°, 29.7±0.5°, 30.5±0.5°, 32.2±0.5° and 37.0±0.5°. A differential scanning calorimetry result shows that heat released at 170° C. is 1098 J/g.

Embodiment 1

Synthesis and test of $(C_6H_{14}N_2)[Na(ClO_4)_3]$

Synthesis Method:
1) adding 112.88 g of 1,4-diazabicyclo[2.2.2]octane into 100 mL of water, then adding 360.00 g of a perchloric acid solution at a mass fraction of 70 to 72 percent, and stirring the mixture at a normal temperature for 5 minutes;

2) adding 140.52 g of monohydrate sodium perchlorate into 50 mL of water, and then stirring at the normal temperature to dissolve the monohydrate sodium perchlorate;

3) mixing the solutions obtained in steps 1) and 2), stirring the mixture for 30 minutes, and then filtering the mixture, washing residues with ethanol for three times, and performing vacuum drying on the washed residues to obtain a white powdery solid which is identified as perovskite type compound $(C_6H_{14}N_2)[Na(ClO_4)_3]$ (No. DAP-1) with a yield of about 80 percent.

Figure 2:
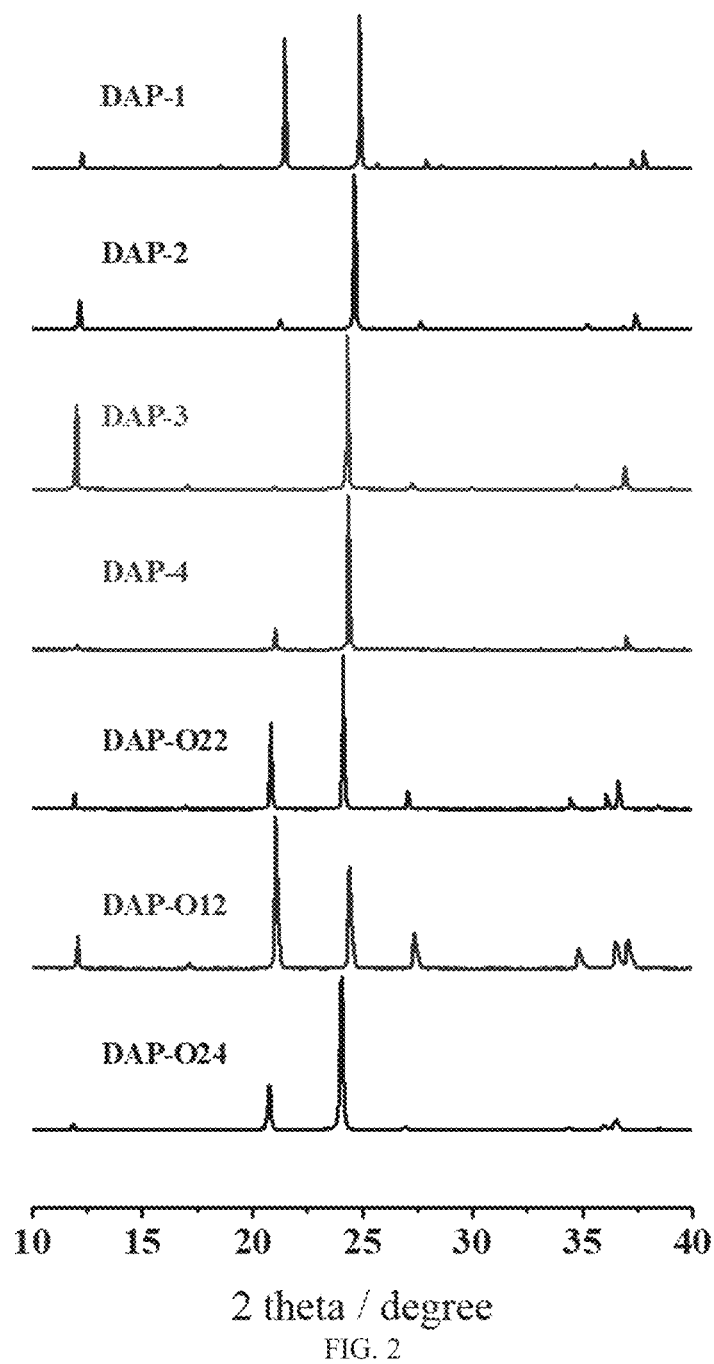
FIG. 2 is a powder X-ray diffraction diagram of energetic compounds according to Embodiments 1 to 7.

A Powder X-Ray Diffraction Identification Diagram:

The powder X-ray diffraction diagram at the room temperature is as shown in FIG. 2, and its characteristic peak values are as shown in Table 1.

TABLE 1

| Characteristic peak values of powder X-ray diffraction of DAP-1 | |
|---|---|
| 2θ/° | d/Å |
| 12.3 | 7.22 |
| 18.6 | 4.78 |
| 21.5 | 4.14 |
| 24.9 | 3.58 |
| 25.7 | 3.47 |
| 27.9 | 3.20 |
| 28.6 | 3.12 |
| 33.8 | 2.65 |
| 35.6 | 2.52 |
| 36.1 | 2.48 |
| 37.2 | 2.41 |
| 37.8 | 2.38 |

Single-Crystal Structure Characterization Test:

Detailed crystal test data are as shown in Table 2. A schematic diagram of a three-dimensional crystal structure is shown in FIG. 1. It can be seen from FIG. 1 that: a Na⁺ ion at a B site is connected with 6 adjacent $ClO_4^-$ anions at X sites, and each $ClO_4^-$ anion is connected with two adjacent Na⁺ ions, thereby forming a three-dimensional anionic framework consisting of cubic cage units. Cavities of each cubic cage unit are filled with organic cations at A sites, namely 1,4-dihydroxy-1,4-diazodicyclo[2.2.2]octane-1,4-diium $(C_6H_{14}N_2^{2+})$.

TABLE 2

| Single-crystal X-ray crystallographic data for DAP-1 | |
|---|---|
| Complex | DAP-1 |
| Formula | $C_6H_{14}Cl_3N_2NaO_{12}$ |
| Formula weight | 435.53 |
| Temperature (K) | 223(2) |
| Crystal system | Cubic |
| Space group | Pa-3 |
| a/Å | 14.1537(1) |
| V/Å³ | 2835.37(4) |
| Z | 8 |
| $D_c$/g cm⁻³ | 2.041 |
| reflections collected | 15434 |
| unique reflections | 1291 |
| $R_{int}$ | 0.0253 |
| $R_1$ [I > 2σ(I)][a] | 0.0259 |
| $wR_2$ [I > 2σ(I)][b] | 0.0681 |

TABLE 2-continued

Single-crystal X-ray crystallographic data for DAP-1

| Complex | DAP-1 |
|---|---|
| $R_1$ (all data) | 0.0304 |
| $wR_2$ (all data) | 0.0714 |
| GOF on $F^2$ | 1.057 |
| Completeness (data) | 0.996 |

Figure 3:
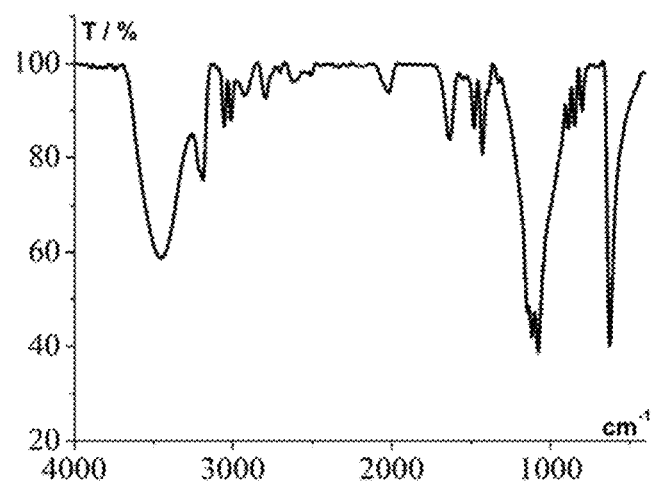
FIG. 3 is an infrared spectrum of energetic compound DAP-1 according to Embodiment 1.

[a]$R_1 = \Sigma||F_o| - |F_c||/\Sigma|F_o|$, [b]$wR_2 = \{\Sigma[w(F_o)^2 - (F_c)^2]^2]/\Sigma w[(F_o)^2]^2\}^{1/2}$ Infrared Spectral Characterization of DAP-1:

An infrared spectrum of DAP-1 is as shown in FIG. 3. It can be seen from FIG. 3 that: characteristic peaks of organic components are stretching vibration peaks 3452, 3188, 3055, 3013, 2924, 2795 and 2706 cm$^{-1}$ of a —CH$_2$— group; the stretching vibration peak of NH$^+$ is 2606 cm$^{-1}$; and the characteristic peaks of a perchlorate radical are asymmetric stretching vibration 1078 cm$^{-1}$ and asymmetric bending vibration 627 cm$^{-1}$.

Figure 4:
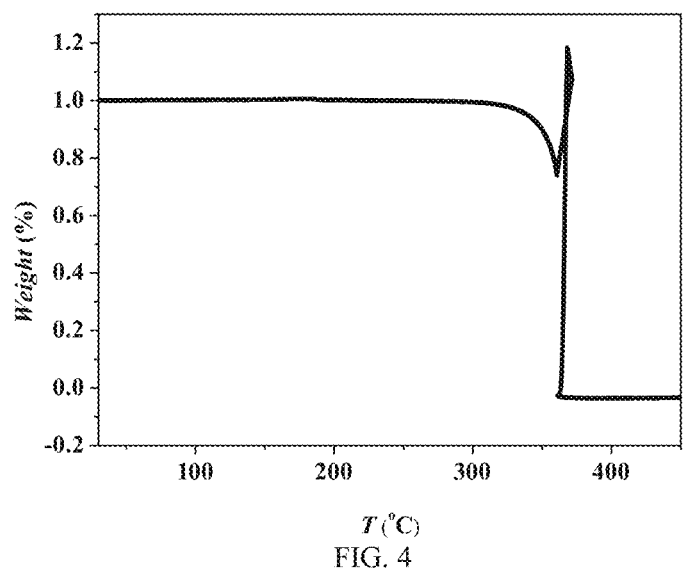
FIG. 4 is a thermogravimetric analysis graph of energetic compound DAP-1 according to Embodiment 1.

Thermal Stability Characterization of DAP-1:

A thermogravimetric curve of DAP-1 is as shown in FIG. 4. It can be seen from FIG. 4 that: under conditions that a sample loading amount is 3.291 mg and a heating rate is 5° C./min, the energetic compound DAP-1 of Embodiment 1 explodes at 360° C.

Figure 5:
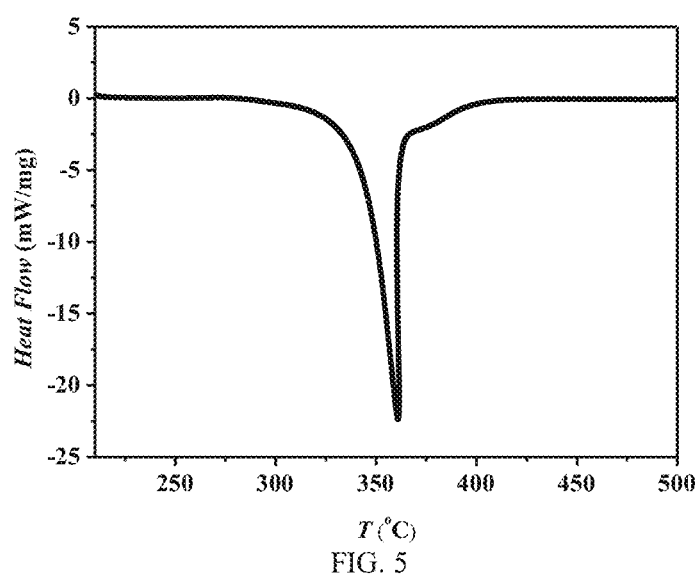
FIG. 5 is a differential scanning calorimetry graph of energetic compound DAP-1 according to Embodiment 1.

Differential Scanning Calorimeter (DSC) of DAP-1:

A DSC curve of DAP-1 is as shown in FIG. 5. It can be seen from FIG. 5 that: the powdery energetic compound DAP-1 in an unloaded state of Embodiment 1 is decomposed at 360° C., and releases a large amount of heat (about 4398 J/g).

Impact, Friction, Thermal and Electrostatic Sensitivity Characterization of DAP-1:

Impact, friction and thermal sensitivity are tested according to the GJB772A-97 standard. The impact sensitivity is tested by a 601.1 explosive probability method. During the test (a hammer weight is 10 kg, and a drop height is 500 mm), the explosive probability of TNT is 9/25, but the explosive probability of DAP-1 is 0 percent. The friction sensitivity is tested by a 602.1 explosive probability method. During the test (2.45 MPa, and a swing angle of 80 degrees), the explosive probability of PETN is 2/25, but the explosive probability of DAP-1 is 0 percent. A thermal sensitivity test method is a 606.1 burst point 5 s-delay method. It measures that DAP-1 dramatically explodes at 340° C., which indicates that the burst point of DAP-1 is 340° C. An electrostatic sensitivity test method is the third section of an industrial initiating explosive material test method WJ/T 9038.3-2004: electrostatic spark sensitivity test. A half trigger voltage $V_{50}$ of 25 mg of the test sample is 4.77 kV (a standard deviation is 0.21 kV), and half trigger energy $E_{50}$ is 0.53 J, namely the electrostatic spark sensitivity of DAP-1 is 21.2 J.

According to a test method of Federal Institute for Material Research and Testing (BAM), the impact sensitivity of DAP-1 is about 17 J, and the friction sensitivity is about 36 N.

Detonation Heat, Detonation Pressure and Detonation Velocity Values of the Energetic Compound DAP-1 are Obtained Theoretically by the DFT:

A decomposition heat value (decomposition enthalpy value $\Delta H_{det}$) of DAP-1 is about 1.53 kcal/g calculated on the basis of the DFT (J. Am. Chem. Soc. 2012, 134, 1422), which is higher than those of active-duty energetic materials HMX (1.26 kcal/g) and RDX (1.27 kcal/g). An energy density is 3.11 kcal/cm$^3$ obtained by conversion of a crystal density at 223 K, which is also higher than those of the active-duty energetic materials HMX (2.38 kcal/cm$^3$) and RDX (2.29 kcal/cm$^3$). According to a Kamlet-Jacob formula, DAP-1 has the detonation velocity of about 8.85 km/s and the detonation pressure of about 37.31 GPa, which are comparable to corresponding values of the active-duty energetic materials (HMX: the detonation velocity of 9.10 km/s and the detonation pressure of 39.50 GPa; RDX: the detonation velocity of 8.80 km/s and the detonation pressure of 33.80 GPa).

The Amount of Gas Produced by DAP-1 Per Mole Number

For judgment on products obtained by complete explosion of the energetic material in an oxygen-free environment, according to a document (J. Am. Chem. Soc. 2012, 134, 1422; J. Phys. Chem. A. 2014, 118, 4575; Chem. Eur. J. 2016, 22, 1141), final decomposition products include gaseous substances such as nitrogen, halogen hydride, water and carbon dioxide, and solid substances such as metal chlorides and elemental carbon (if oxygen atoms are not enough to completely convert all carbon atoms into the carbon dioxide). Therefore, 1 mole of DAP-1 may produce 12 moles of gas substances after complete explosion in the oxygen-free environment, with 3 moles of elemental carbon and 1 mole of solid sodium chloride remaining. Under a condition that an enough amount of oxidant (such as commonly used NH$_4$ClO$_4$) is mixed, DAP-1 per mole produces 1 mole of solid sodium chloride residues after complete explosion.

Embodiment 2

Synthesis and test of (C$_6$H$_{14}$N$_2$)[K(ClO$_4$)$_3$]

Synthesis Method:
1) adding 2.24 g of 1,4-diazabicyclo[2.2.2]octane into 100 mL of water, then adding 5.74 g of a perchloric acid solution at a mass fraction of 70 to 72 percent, and stirring the mixture at a normal temperature for 5 minutes;
2) adding 2.77 of potassium perchlorate into 100 mL of water, and then heating and stirring the mixture to dissolve the potassium perchlorate.
3) mixing the solutions obtained in steps 1) and 2), stirring the mixture for 30 minutes, filtering the mixture, washing residues with ethanol for three times, and performing vacuum drying on washed residues to obtain a white powdery solid that is identified as perovskite type compound (C$_6$H$_{14}$N$_2$)[K(ClO$_4$)$_3$] (No. DAP-2) with the yield of about 90 percent.

A Powder X-Ray Diffraction Identification Diagram:

The powder X-ray diffraction diagram at the room temperature is as shown in FIG. 2, and its characteristic peak values are as shown in Table 3.

TABLE 3

Characteristic peak values of Powder X-ray diffraction of DAP-2

| 2θ/° | d/Å |
|---|---|
| 11.9 | 7.43 |
| 12.2 | 7.28 |
| 17.3 | 5.12 |
| 21.3 | 4.17 |
| 23.8 | 3.73 |
| 24.63 | 3.61 |
| 27.6 | 3.23 |
| 35.2 | 2.55 |

TABLE 3-continued

Characteristic peak values of Powder X-ray diffraction of DAP-2

| 2θ/° | d/Å |
|---|---|
| 36.9 | 2.43 |
| 37.4 | 2.40 |

Single-Crystal Structure Characterization Test:
Detailed crystal test data are as shown in Table 4.

TABLE 4

Single-crystal X-ray crystallographic data for DAP-2

| Complex | DAP-2 |
|---|---|
| Formula | $C_6H_{14}Cl_3N_2KO_{12}$ |
| Formula weight | 451.64 |
| Temperature (K) | 223(2) |
| Crystal system | Cubic |
| Space group | Pa-3 |
| a/Å | 14.2910(1) |
| V/Å$^3$ | 2918.69(4) |
| Z | 8 |
| $D_c$/g cm$^{-3}$ | 2.056 |
| reflections collected | 5749 |
| unique reflections | 1254 |
| $R_{int}$ | 0.0348 |
| $R_1$ [I > 2σ(I)]$^{[a]}$ | 0.0285 |
| $wR_2$ [I > 2σ(I)]$^{[b]}$ | 0.0691 |
| $R_1$ (all data) | 0.0394 |
| $wR_2$ (all data) | 0.0761 |
| GOF on $F^2$ | 1.100 |
| Completeness (data) | 0.999 |

Figure 6:
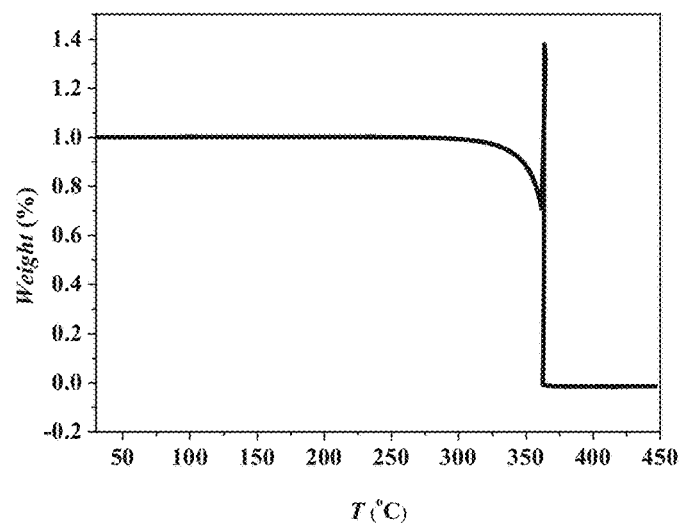
FIG. 6 is a thermogravimetric analysis graph of energetic compound DAP-2 according to Embodiment 2.

$^{[a]}R_1 = \Sigma||F_o| - |F_c||/\Sigma|F_o|$, $^{[b]}wR_2 = \{\Sigma[w(F_o)^2 - (F_c)^2]^2/\Sigma w[(F_o)^2]^2\}^{1/2}$ Thermal Stability Characterization of DAP-2:

A thermogravimetric curve of DAP-2 is as shown in FIG. 6. It can be seen from FIG. 6 that: under conditions that a sample loading amount is 6.65 mg and a heating rate is 5° C./min, the energetic compound DAP-2 of Embodiment 2 explodes at 362° C.

Figure 7:
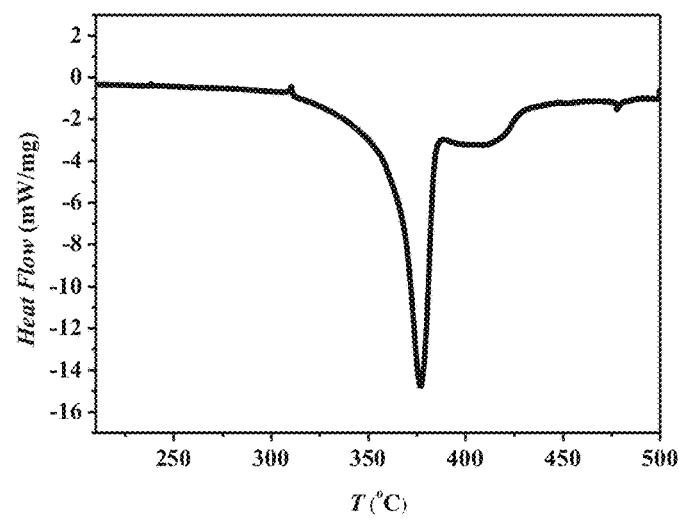
FIG. 7 is a differential scanning calorimetry graph of energetic compound DAP-2 according to Embodiment 2.

Differential Scanning Calorimeter (DSC) of DAP-2:

A DSC curve of DAP-2 is as shown in FIG. 7. It can be seen from FIG. 7 that: the powdery energetic compound DAP-2 in an unloaded state of Embodiment 2 is decomposed at 377° C., and releases a large amount of heat (about 4076 J/g).

Impact and Friction Sensitivity Characterization of DAP-2:

According to a test method of a Federal Institute for Material Research and Testing (BAM), the impact sensitivity of DAP-2 is about 16 J, and the friction sensitivity is about 42 N.

Detonation Heat, Detonation Pressure and Detonation Velocity Values of the Energetic Compound DAP-2 Obtained Theoretically by the DFT:

A decomposition heat value (decomposition enthalpy value $\Delta H_{det}$) of DAP-2 is about 1.46 kcal/g calculated on the basis of the DFT (J. Am. Chem. Soc. 2012, 134, 1422), which is higher than those of active-duty energetic materials HMX (1.26 kcal/g) and RDX (1.27 kcal/g). An energy density is 3.01 kcal/cm$^3$ obtained by conversion of a crystal density at 223 K, which is also higher than those of the active-duty energetic materials HMX (2.38 kcal/cm$^3$) and RDX (2.29 kcal/cm$^3$). According to a Kamlet-Jacob formula, DAP-2 has the detonation velocity of about 8.64 km/s and the detonation pressure of about 35.73 GPa.

The Amount of Gas Produced by DAP-2 Per Mole Number

For judgment on products obtained by complete explosion of the energetic material in an oxygen-free environment, according to a document (J. Am. Chem. Soc. 2012, 134, 1422; J. Phys. Chem. A. 2014, 118, 4575; Chem. Eur. J. 2016, 22, 1141), final decomposition products include gaseous substances such as nitrogen, halogen hydride, water and carbon dioxide, and solid substances such as metal chlorides and elemental carbon (if oxygen atoms are not enough to completely convert all carbon atoms into the carbon dioxide). Therefore, 1 mole of DAP-2 may produce 12 moles of gas substances after complete explosion in the oxygen-free environment, with 3 moles of elemental carbon and 1 mole of solid potassium chloride remaining. Under a condition that an enough amount of oxidant (such as commonly used $NH_4ClO_4$) is mixed, DAP-2 per mole produces 1 mole of solid potassium chloride residues after complete explosion.

Embodiment 3

Synthesis and test of $(C_6H_{14}N_2)[Rb(ClO_4)_3]$

Synthesis Method:
1) adding 2.24 g of 1,4-diazabicyclo[2.2.2]octane into 100 mL of water, then adding 5.74 g of a perchloric acid solution at a mass fraction of 70 to 72 percent, and stirring the mixture at a normal temperature for 5 minutes;
2) adding 3.70 of rubidium perchlorate into 100 mL of water, and then heating and stirring the mixture to dissolve the rubidium perchlorate;
3) mixing the solutions obtained in steps 1) and 2), stirring the mixture for 30 minutes, filtering the mixture, washing residues with ethanol for three times, and performing vacuum drying on the washed residues to obtain a white powdery solid that is identified as perovskite type compound $(C_6H_{14}N_2)[Rb(ClO_4)_3]$ (No. DAP-3) with the yield of about 85 percent.

A Powder X-Ray Diffraction Identification Diagram:

The powder X-ray diffraction diagram at the room temperature is as shown in FIG. 2, and its characteristic peak values are as shown in Table 5.

TABLE 5

Characteristic peak values of powder X-ray diffraction of DAP-3

| 2θ/° | d/Å |
|---|---|
| 12.0 | 7.36 |
| 17.1 | 5.19 |
| 21.0 | 4.23 |
| 23.6 | 3.77 |
| 24.3 | 3.66 |
| 27.3 | 3.27 |
| 27.0 | 2.98 |
| 34.7 | 2.58 |
| 36.4 | 2.47 |
| 36.9 | 2.43 |
| 39.0 | 2.31 |

Single-Crystal Structure Characterization Test:
Detailed crystal test data are as shown in Table 6.

TABLE 6

Single-crystal X-ray crystallographic data for DAP-3

| Complex | DAP-3 |
|---|---|
| Formula | $C_6H_{14}Cl_3N_2RbO_{12}$ |
| Formula weight | 498.01 |

TABLE 6-continued

Single-crystal X-ray crystallographic data for DAP-3

| Complex | DAP-3 |
|---|---|
| Temperature (K) | 223(2) |
| Crystal system | Cubic |
| Space group | Pa-3 |
| a/Å | 14.453(2) |
| V/Å$^3$ | 3018.9(7) |
| Z | 8 |
| $D_c$/g cm$^{-3}$ | 2.191 |
| reflections collected | 14540 |
| unique reflections | 978 |
| $R_{int}$ | 0.0463 |
| $R_1$ [I > 2σ(I)][a] | 0.0254 |
| $wR_2$ [I > 2σ(I)][b] | 0.0669 |
| $R_1$ (all data) | 0.0262 |
| $wR_2$ (all data) | 0.0676 |
| GOF on F$^2$ | 1.078 |
| Completeness (data) | 0.996 |

Figure 8:
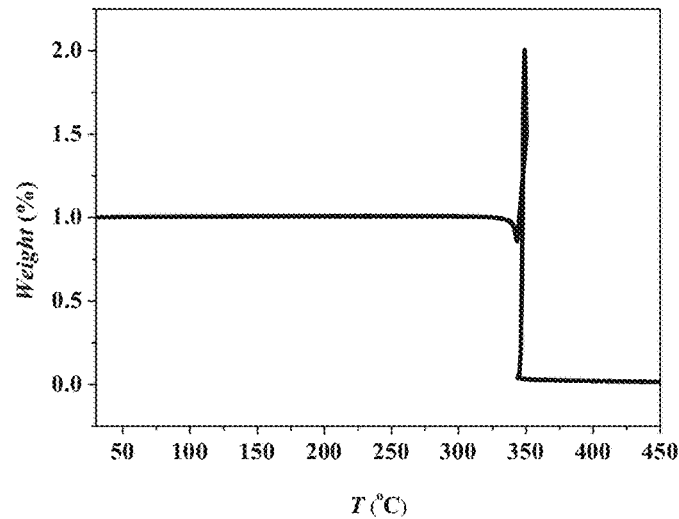
FIG. 8 is a thermogravimetric analysis graph of energetic compound DAP-3 according to Embodiment 3.

[a]$R_1 = \Sigma||F_o| - |F_c||/\Sigma|F_o|$, [b]$wR_2 = \{\Sigma[w(F_o)^2 - (F_c)^2]^2/\Sigma[w(F_o)^2]^2\}^{1/2}$ Thermal Stability Characterization of DAP-3:

A thermogravimetric curve of DAP-3 is as shown in FIG. 8. It can be seen from FIG. 8 that: under conditions that a sample loading amount is 4.45 mg and a heating rate is 5° C./min, the energetic compound DAP-3 of Embodiment 3 explodes at 343° C.

Figure 9:
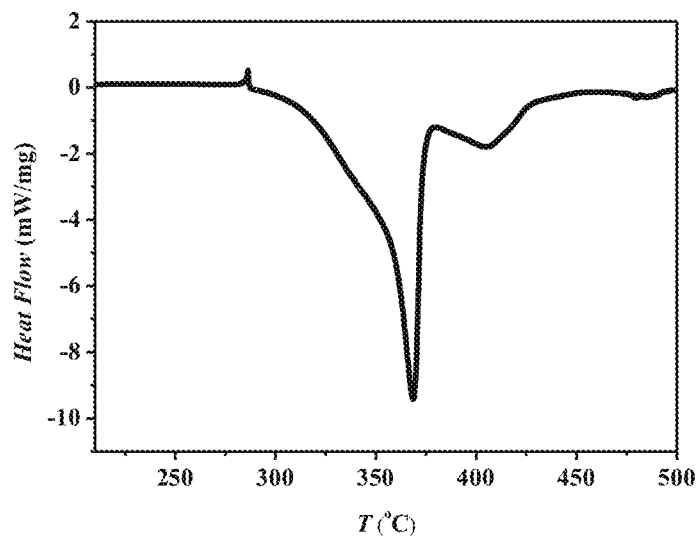
FIG. 9 is a differential scanning calorimetry graph of energetic compound DAP-3 according to Embodiment 3.

Differential Scanning Calorimeter (DSC) of DAP-3:

A DSC curve of DAP-3 is as shown in FIG. 9. It can be seen from FIG. 9 that: the powdery energetic compound DAP-3 in an unloaded state of Embodiment 3 is decomposed at 369° C., and releases a large amount of heat (about 3797 J/g).

Impact and Friction Sensitivity Characterization of DAP-3:

According to a test method of a Federal Institute for Material Research and Testing (BAM), the impact sensitivity of DAP-3 is about 22 J, and the friction sensitivity is about 28 N.

Detonation Heat, Detonation Pressure and Detonation Velocity Values of the Energetic Compound DAP-3 Obtained Theoretically by the DFT:

A decomposition heat value (decomposition enthalpy value $\Delta H_{det}$) of DAP-3 is about 1.33 kcal/g calculated on the basis of the DFT (J. Am. Chem. Soc. 2012, 134, 1422), which is higher than those of active-duty energetic materials HMX (1.26 kcal/g) and RDX (1.27 kcal/g). An energy density is 2.92 kcal/cm$^3$ obtained by conversion of a crystal density at 223 K, which is also higher than those of the active-duty energetic materials HMX (2.38 kcal/cm$^3$) and RDX (2.29 kcal/cm$^3$). According to a Kamlet-Jacob formula, DAP-3 has the detonation velocity of about 8.43 km/s and the detonation pressure of about 35.14 GPa.

The Amount of Gas Produced by DAP-3 Per Mole Number

For judgment on products obtained by complete explosion of the energetic material in an oxygen-free environment, according to a document (J. Am. Chem. Soc. 2012, 134, 1422; J. Phys. Chem. A. 2014, 118, 4575; Chem. Eur. J. 2016, 22, 1141), final decomposition products include gaseous substances such as nitrogen, halogen hydride, water and carbon dioxide, and solid substances such as metal chlorides and elemental carbon (if oxygen atoms are not enough to completely convert all carbon atoms into the carbon dioxide). Therefore, 1 mole of DAP-3 may produce 12 moles of gas substances after complete explosion in the oxygen-free environment, with 3 moles of elemental carbon and 1 mole of solid rubidium chloride remaining. Under a condition that an enough amount of oxidant (such as commonly used $NH_4ClO_4$) is mixed, DAP-3 per mole produces 1 mole of solid rubidium chloride residues after complete explosion.

Embodiment 4

Synthesis and test of $(C_6H_{14}N_2)[NH_4(ClO_4)_3]$

Synthesis Method:

1) adding 2.24 g of 1,4-diazabicyclo[2.2.2]octane into 5 mL of water, then adding 5.74 g of a perchloric acid solution at a mass fraction of 70 to 72 percent, and stirring the mixture at a normal temperature for 5 minutes;
2) adding 2.35 g of ammonium perchlorate into 10 mL of water, and then stirring the mixture at the normal temperature to dissolve the ammonium perchlorate;
3) mixing the solutions obtained in steps 1) and 2), stirring the mixture for 10 minutes, filtering the mixture, washing residues with ethanol for three times, and performing vacuum drying on washed residues to obtain a white powdery solid that is identified as perovskite type compound $(C_6H_{14}N_2)[NH_4(ClO_4)_3]$ (No. DAP-4) with the yield of about 90 percent.

A Powder X-Ray Diffraction Identification Diagram:

The powder X-ray diffraction diagram at the room temperature is as shown in FIG. 2, and its characteristic peak values are as shown in Table 7.

TABLE 7

Characteristic peak values of powder X-ray diffraction of DAP-4

| 2θ/° | d/Å |
|---|---|
| 12.0 | 7.35 |
| 21.0 | 4.22 |
| 22.0 | 4.05 |
| 23.5 | 3.78 |
| 23.7 | 3.75 |
| 24.4 | 3.65 |
| 27.3 | 3.26 |
| 34.8 | 2.58 |
| 36.5 | 2.46 |
| 37.0 | 2.43 |

Single-Crystal Structure Characterization Test:

Detailed crystal test data are as shown in Table 8.

TABLE 8

Crystal test data of DAP-4

| Complex | DAP-4 |
|---|---|
| Formula | $C_6H_{18}Cl_3N_3O_{12}$ |
| Formula weight | 430.56 |
| Temperature (K) | 223(2) |
| Crystal system | Cubic |
| Space group | Pa-3 |
| a/Å | 14.4264(1) |
| V/Å$^3$ | 3002.44(4) |
| Z | 8 |
| $D_c$/g cm$^{-3}$ | 1.887 |
| reflections collected | 13016 |
| unique reflections | 1609 |
| $R_{int}$ | 0.0353 |
| $R_1$ [I > 2σ(I)][a] | 0.0323 |
| $wR_2$ [I > 2σ(I)][b] | 0.1127 |
| $R_1$ (all data) | 0.0378 |
| $wR_2$ (all data) | 0.1167 |

TABLE 8-continued

Crystal test data of DAP-4

| Complex | DAP-4 |
|---|---|
| GOF on $F^2$ | 0.9792 |
| Completeness (data) | 1.000 |

Figure 10:
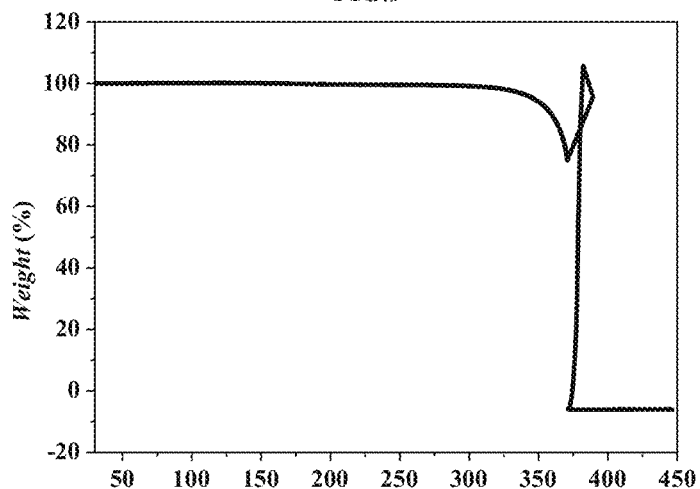
FIG. 10 is a thermogravimetric analysis graph of energetic compound DAP-4 according to Embodiment 4.

[a]$R_1 = \Sigma||F_o| - |F_c||/\Sigma|F_o|$, [b]$wR_2 = \{\Sigma w[(F_o)^2 - (F_c)^2]^2/\Sigma w[(F_o)^2]\}^{1/2}$ Thermal Stability Characterization of DAP-4:

A thermogravimetric curve of DAP-4 is as shown in FIG. 10. It can be seen from FIG. 10 that: under conditions that a sample loading amount is 4.825 mg and a heating rate is 5° C./min, the energetic compound DAP-4 of Embodiment 4 explodes at 370° C.

Figure 11:
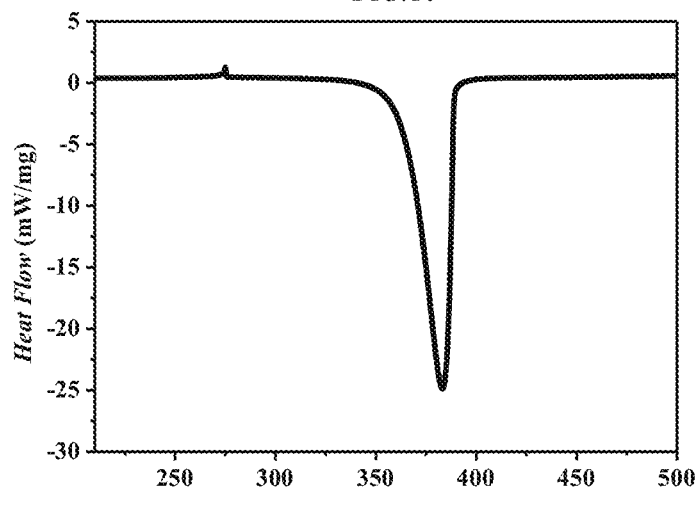
FIG. 11 is a differential scanning calorimetry graph of energetic compound DAP-4 according to Embodiment 4.

Differential Scanning Calorimeter (DSC) of DAP-4:

A DSC curve of DAP-4 is as shown in FIG. 11. It can be seen from FIG. 11 that: the powdery energetic compound DAP-4 in an unloaded state of Embodiment 4 is decomposed at 364° C., and releases a large amount of heat (about 5177 J/g).

Impact and Friction Sensitivity Characterization of DAP-4:

According to a test method of a Federal Institute for Material Research and Testing (BAM), the impact sensitivity of DAP-4 is about 23 J, and the friction sensitivity is about 36 N.

The Amount of Gas Produced by DAP-4 Per Mole Number

For judgment on products obtained by complete explosion of the energetic material in an oxygen-free environment, according to a document (J. Am. Chem. Soc. 2012, 134, 1422; J. Phys. Chem. A. 2014, 118, 4575; Chem. Eur. J. 2016, 22, 1141), final decomposition products include gaseous substances such as nitrogen, halogen hydride, water and carbon dioxide, and solid substances such as elemental carbon (if oxygen atoms are not enough to completely convert all carbon atoms into the carbon dioxide). Therefore, 1 mole of DAP-4 may produce 14.25 moles of gas substances after complete explosion in the oxygen-free environment, with 3.75 moles of elemental carbon remaining. Under a condition that an enough amount of oxidant (such as commonly used $NH_4ClO_4$) is mixed, DAP-4 produces no solid residues after complete explosion.

Embodiment 5

Synthesis and test of $(C_6H_{14}N_2O_2)[K(ClO_4)_3]$

Synthesis Method:
1) putting 1.01 g of 1,4-diazabicyclo[2.2.2]octane into a flask, gradually adding 6.0 g of hydrogen peroxide at a mass fraction of 30 percent for full reaction, thus obtaining an aqueous solution of 1,4-diazabicyclo[2.2.2]octane 1,4-dioxide, then adding 2.64 g of a perchloric acid solution at a mass fraction of 70 to 72 percent, and stirring the mixture for 20 minutes;
2) adding 0.42 g of potassium perchlorate into 20 mL of water, then heating the mixture until it is boiling, and stirring the mixture to dissolve the potassium perchlorate;
3) mixing the solutions obtained in steps 1) and 2), stirring the mixture for 10 minutes, and standing the mixture to gradually produce crystals; filtering the crystals, and washing residues with ethanol for three times; and performing vacuum drying on washed residues to obtain a white powdery solid that is identified as perovskite type compound $(C_6H_{14}N_2O_2)[K(ClO_4)_3]$ (DAP-O22) at the yield of about 55 percent.

A Powder X-Ray Diffraction Identification Diagram:

The powder X-ray diffraction diagram at the room temperature is as shown in FIG. 2, and its characteristic peak values are as shown in Table 9.

TABLE 9

Characteristic peak values of powder X-ray diffraction of DAP-O22

| 2θ/° | d/Å |
|---|---|
| 11.9 | 7.41 |
| 17.0 | 5.22 |
| 20.8 | 4.26 |
| 24.1 | 3.69 |
| 27.0 | 3.29 |
| 28.2 | 3.16 |
| 34.4 | 2.60 |
| 36.1 | 2.49 |
| 36.6 | 2.45 |
| 38.4 | 2.34 |

Single-Crystal Structure Characterization Test:

Detailed crystal test data are as shown in Table 10.

TABLE 10

Crystal test data of DAP-O22

| Complex | DAP-O22 |
|---|---|
| Formula | $C_6H_{14}Cl_3N_2KO_{14}$ |
| Formula weight | 469.53 |
| Temperature (K) | 298(2) |
| Crystal system | Cubic |
| Space group | Fm-3c |
| a/Å | 14.745(3) |
| V/Å$^3$ | 3205.78 |
| Z | 8 |
| $D_c$/g cm$^{-3}$ | 1.946 |
| reflections collected | 606 |
| unique reflections | 154 |
| $R_{int}$ | 0.0265 |
| $R_1$ [I > 2σ(I)][a] | 0.0427 |
| $wR_2$ [I > 2σ(I)][b] | 0.1022 |
| $R_1$ (all data) | 0.0658 |
| $wR_2$ (all data) | 0.1172 |
| GOF on $F^2$ | 1.066 |
| Completeness (data) | 0.911 |

Figure 12:
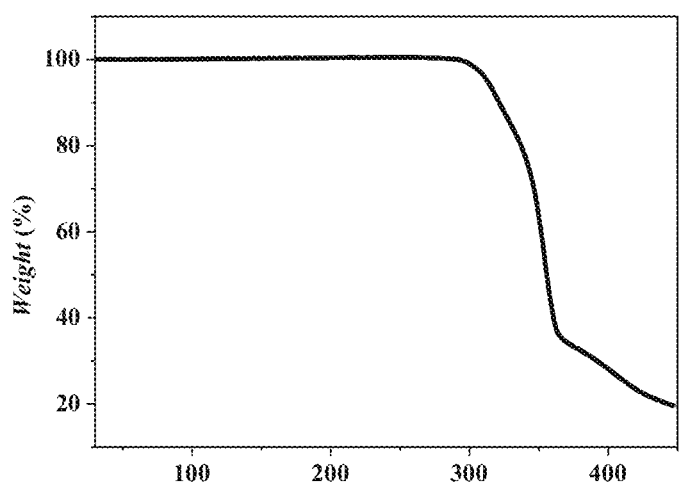
FIG. 12 is a thermogravimetric analysis graph of energetic compound DAP-O22 according to Embodiment 5.

[a]$R_1 = \Sigma||F_o| - |F_c||/\Sigma|F_o|$, [b]$wR_2 = \{\Sigma w[(F_o)^2 - (F_c)^2]^2/\Sigma w[(F_o)^2]\}^{1/2}$ Thermal Stability Characterization of DAP-O22:

A thermogravimetric curve of DAP-O22 is as shown in FIG. 12. It can be seen from FIG. 12 that: under conditions that a sample loading amount is 4.175 mg and a heating rate is 5° C./min, the energetic compound DAP-O22 of Embodiment 5 is decomposed at 354° C.

Figure 13:
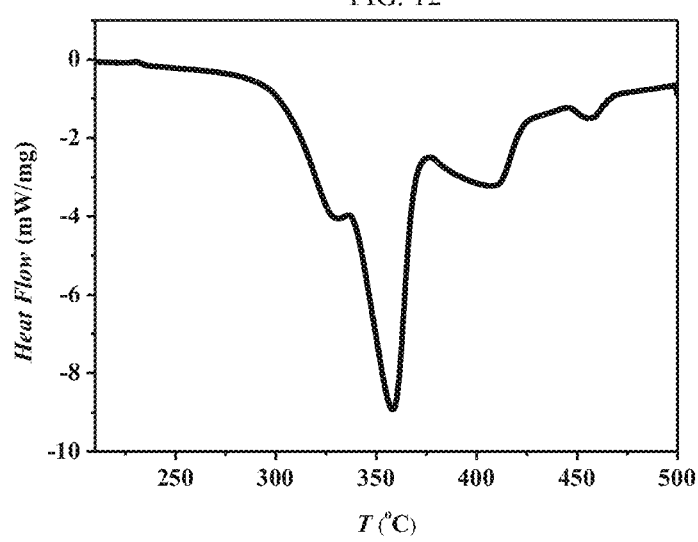
FIG. 13 is a differential scanning calorimetry graph of energetic compound DAP-O22 according to Embodiment 5.

Differential Scanning Calorimeter (DSC) of DAP-O22:

A DSC curve of DAP-O22 is as shown in FIG. 13. It can be seen from FIG. 13 that: the powdery energetic compound DAP-O22 in an unloaded state of Embodiment 5 is decomposed at 358° C., and releases a large amount of heat (about 5424 J/g).

Impact and Friction Sensitivity Characterization of DAP-O22:

According to a test method of a Federal Institute for Material Research and Testing (BAM), the impact sensitivity of DAP-O22 is about 11 J, and the friction sensitivity is about 14 N.

The Amount of Gas Produced by DAP-O22 Per Mole Number

For judgment on products obtained by complete explosion of the energetic material in an oxygen-free environment, according to a document (J. Am. Chem. Soc. 2012, 134, 1422; *J. Phys. Chem. A.* 2014, 118, 4575; *Chem. Eur. J.* 2016, 22, 1141), final decomposition products include gaseous substances such as nitrogen, halogen hydride, water and carbon dioxide, and solid substances such as metal chlorides and elemental carbon (if oxygen atoms are not enough to completely convert all carbon atoms into the carbon dioxide). Therefore, 1 mole of DAP-O22 may produce 13 moles of gas substances after complete explosion in the oxygen-free environment, with 2 moles of elemental carbon and 1 mole of solid potassium chloride remaining. Under a condition that an enough amount of oxidant (such as commonly used $NH_4ClO_4$) is mixed, DAP-O22 per mole produces 1 mole of solid potassium chloride residues after complete explosion.

Embodiment 6

Synthesis and test of $(C_6H_{14}N_2O)[K(ClO_4)_3]$

Synthesis Method:
1) putting 1.01 g of 1,4-diazabicyclo[2.2.2]octane into a flask for continuous ice bathing, gradually and slowly adding 2.0 g of hydrogen peroxide at a mass fraction of 30 percent, thus obtaining an aqueous solution of 1,4-diazabicyclo[2.2.2]octane 1-oxide, then adding 2.64 g of a perchloric acid solution at a mass fraction of 70 to 72 percent, and stirring the mixture for 20 minutes;
2) adding 0.42 g of potassium perchlorate into 20 mL of water, then heating the mixture until it is boiling, and stirring the mixture to dissolve the potassium perchlorate;
3) mixing the solutions obtained in steps 1) and 2), stirring the mixture for 10 minutes and standing the mixture to gradually produce crystals; filtering the crystals, and washing residues with ethanol for three times, and performing vacuum drying on the washed residues to obtain a white powdery solid that is identified as perovskite type compound $(C_6H_{14}N_2O)[K(ClO_4)_3]$ (DAP-O12) with the yield of about 30 percent.

A Powder X-Ray Diffraction Identification Graph:

The powder X-ray diffraction graph at the room temperature is as shown in FIG. 2, and its characteristic peak values are as shown in Table 11.

TABLE 11

| Characteristic peak values of powder X-ray diffraction of DAP-O12 | |
|---|---|
| 2θ/° | d/Å |
| 12.1 | 7.33 |
| 17.1 | 5.18 |
| 21.1 | 4.22 |
| 24.4 | 3.64 |
| 27.3 | 3.26 |
| 28.2 | 3.17 |
| 34.8 | 2.58 |
| 36.5 | 2.46 |
| 37.1 | 2.42 |
| 38.4 | 2.34 |
| 39.8 | 2.26 |

The Amount of Gas Produced by DAP-O12 Per Mole Number

For judgment on products obtained by complete explosion of the energetic material in an oxygen-free environment, according to a document (*J. Am. Chem. Soc.* 2012, 134, 1422; *J. Phys. Chem. A.* 2014, 118, 4575; *Chem. Eur. J.* 2016, 22, 1141), final decomposition products include gaseous substances such as nitrogen, halogen hydride, water and carbon dioxide, and solid substances such as metal chlorides and elemental carbon (if oxygen atoms are not enough to completely convert all carbon atoms into the carbon dioxide). Therefore, 1 mole of DAP-O12 may produce 12.5 moles of gas substances after complete explosion in the oxygen-free environment, with 2.5 moles of elemental carbon and 1 mole of solid potassium chloride remaining. Under a condition that an enough amount of oxidant (such as commonly used $NH_4ClO_4$) is mixed, DAP-O12 per mole produces 1 mole of solid potassium chloride residues after complete explosion.

Embodiment 7

Synthesis and test of $(C_6H_{14}N_2O_2)[NH_4(ClO_4)_3]$

Synthesis Method:
1) putting 0.34 g of 1,4-diazabicyclo[2.2.2]octane into a flask, gradually and slowly adding 0.69 g of hydrogen peroxide at a mass fraction of 30 percent at a normal temperature, thus obtaining an aqueous solution of 1,4-diazabicyclo[2.2.2]octane 1,4-dioxide, then adding 0.86 g of a perchloric acid solution at a mass fraction of 70 to 72 percent, and stirring the mixture for 20 minutes;
2) adding 0.41 g of potassium perchlorate into 20 mL of water, stirring the mixture to dissolve the potassium perchlorate;
3) mixing the solutions obtained in steps 1) and 2), stirring the mixture for 10 minutes, and standing the mixture to gradually produce crystals; filtering the crystals, and washing residues with ethanol for three times; and performing vacuum drying on the washed residues to obtain a white powdery solid that is identified as perovskite type compound $(C_6H_{14}N_2O_2)[NH_4(ClO_4)_3]$ (DAP-O24) at the yield of about 30 percent.

A Powder X-Ray Diffraction Identification Diagram:

The powder X-ray diffraction diagram at the room temperature is as shown in FIG. 2, and its characteristic peak values are as shown in Table 12.

TABLE 12

| Characteristic peak values of powder X-ray diffraction of DAP-O24 | |
|---|---|
| 2θ/° | d/Å |
| 11.9 | 7.46 |
| 20.8 | 4.27 |
| 23.4 | 3.80 |
| 24.0 | 3.70 |
| 27.0 | 3.30 |
| 29.6 | 3.02 |
| 34.4 | 2.61 |
| 36.0 | 2.49 |
| 36.5 | 2.46 |
| 38.4 | 2.34 |

Figure 14:
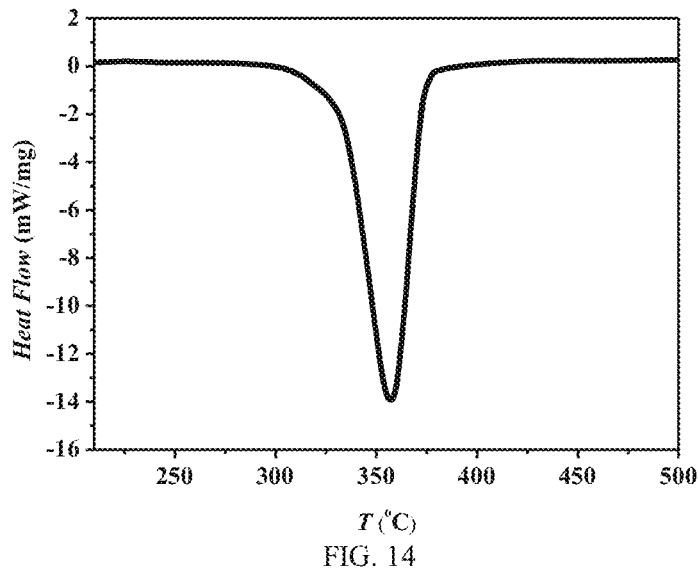
FIG. 14 is a differential scanning calorimetry graph of energetic compound DAP-O24 according to Embodiment 7.

Differential Scanning Calorimeter (DSC) of DAP-O24:

A DSC curve of DAP-O24 is as shown in FIG. 14. It can be seen from FIG. 14 that: the powdery energetic compound DAP-O24 in an unloaded state of Embodiment 7 is decomposed at 357° C., and releases a large amount of heat (about 4632 J/g).

Impact and Friction Sensitivity Characterization of DAP-O24:

According to a test method of a Federal Institute for Material Research and Testing (BAM), the impact sensitivity of DAP-O24 is about 4 J, and the friction sensitivity is about 32 N.

The Amount of Gas Produced by DAP-O24 Per Mole Number

For judgment on products obtained by complete explosion of the energetic material in an oxygen-free environment, according to a document (*J. Am. Chem. Soc.* 2012, 134, 1422; *J. Phys. Chem. A.* 2014, 118, 4575; *Chem. Eur. J.* 2016, 22, 1141), final decomposition products include gaseous substances such as nitrogen, halogen hydride, water and carbon dioxide, and solid substances such as elemental carbon (if oxygen atoms are not enough to completely convert all carbon atoms into the carbon dioxide). Therefore, 1 mole of DAP-O24 may produce 15.25 moles of gas substances after complete explosion in the oxygen-free environment, with 2.75 moles of elemental carbon remaining. Under a condition that an enough amount of oxidant (such as commonly used $NH_4ClO_4$) is mixed, DAP-O24 produces no solid residues after complete explosion.

Embodiment 8

Synthesis and test of $(C_4H_{12}N_2)[Na(ClO_4)_3]$

Synthesis Method:
1) adding 0.87 g of piperazine into 6 mL of water, then adding 1.7 mL of a perchloric acid solution at a mass fraction of 70 to 72 percent, and stirring the mixture at a normal temperature for 5 minutes;
2) adding 1.24 g of sodium perchlorate into 7 mL of water, stirring the mixture at the normal temperature to dissolve the sodium perchlorate;
3) mixing the solutions obtained in steps 1) and 2); heating the mixture to concentrate it; stirring the concentrated mixture for 30 minutes; filtering the mixture, and washing residues with ethanol for three times; and performing vacuum drying on the residues to obtain a white powdery solid that is identified as perovskite type compound $(C_4H_{12}N_2)[Na(ClO_4)_3]$ (No. PAP-1) with the yield of about 50 percent.

Figure 15:
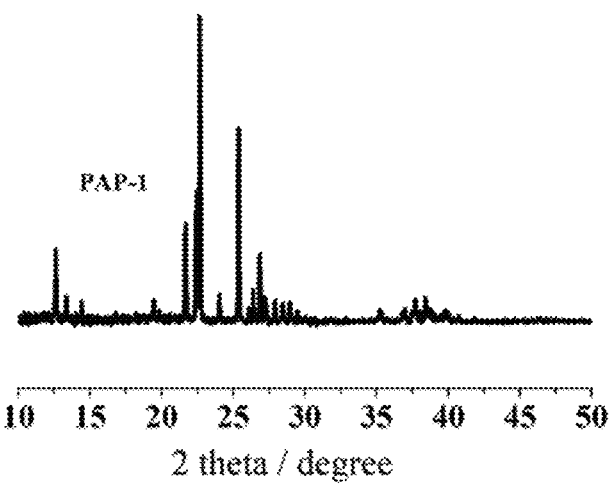
FIG. 15 is a powder X-ray diffraction diagram of energetic compound PAP-1 according to Embodiment 8.

A Powder X-Ray Diffraction Identification Diagram:

The powder X-ray diffraction diagram at the room temperature is as shown in FIG. 15, and its characteristic peak values are as shown in Table 13.

TABLE 13

Characteristic peak values of powder X-ray diffraction of PAP-1

| 2θ/° | d/Å |
|---|---|
| 12.6 | 7.01 |
| 21.7 | 4.09 |
| 22.4 | 3.96 |
| 22.7 | 3.92 |
| 24.0 | 3.70 |
| 25.4 | 3.51 |
| 26.8 | 3.32 |
| 27.2 | 3.27 |
| 37.7 | 2.38 |
| 38.4 | 2.34 |

Single-Crystal Structure Characterization Test:
Detailed crystal test data are as shown in Table 14.

TABLE 14

Crystal test data of PAP-1

| Complex | PAP-1 |
|---|---|
| Formula | $C_4H_{12}Cl_3N_2NaO_{12}$ |
| Formula weight | 409.49 |
| Temperature (K) | 298(2) |
| Crystal system | Monoclinic |
| Space group | $P2_1/c$ |
| a/Å | 10.1689(4) |
| b/Å | 9.7312(4) |
| c/Å | 13.2985(6) |
| β/° | 91.993(4) |
| V/Å$^3$ | 1315.17(9) |
| Z | 4 |
| $D_c$/g cm$^{-3}$ | 2.068 |
| reflections collected | 11329 |
| unique reflections | 2722 |
| $R_{int}$ | 0.1187 |
| $R_1$ [I > 2σ(I)][a] | 0.0731 |
| $wR_2$ [I > 2σ(I)][b] | 0.2007 |
| $R_1$ (all data) | 0.0788 |
| $wR_2$ (all data) | 0.2103 |
| GOF on F$^2$ | 1.0292 |
| Completeness (data) | 0.9742 |

Figure 16:
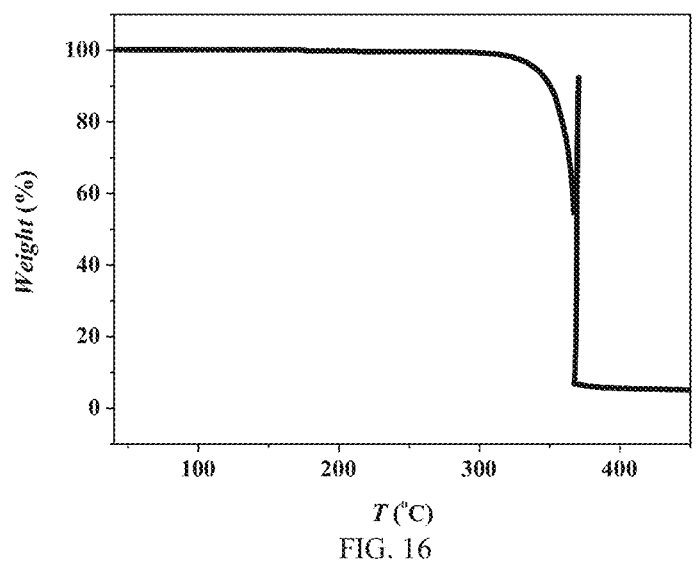
FIG. 16 is a thermogravimetric analysis graph of energetic compound PAP-1 according to Embodiment 8.

[a]$R_1 = \Sigma||F_o| - |F_c||/\Sigma|F_o|$, [b]$wR_2 = \{\Sigma w[(F_o)^2 - (F_c)^2]^2/\Sigma w[(F_o)^2]\}^{1/2}$ Thermal Stability Characterization of PAP-1:

A thermogravimetric curve of PAP-1 is as shown in FIG. 16. It can be seen from FIG. 16 that: under conditions that a sample loading amount is 2.23 mg and a heating rate is 5° C./min, the energetic compound PAP-1 of Embodiment 8 explodes at 367° C.

Figure 17:
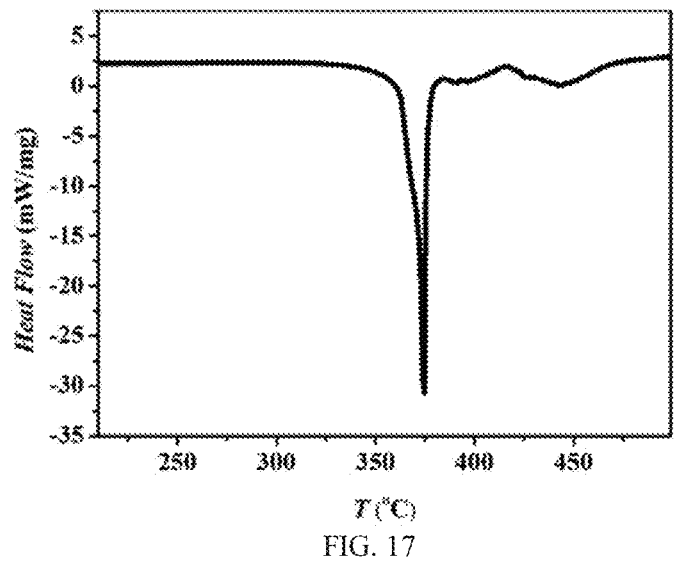
FIG. 17 is a differential scanning calorimetry graph of energetic compound PAP-1 according to Embodiment 8.

Differential Scanning Calorimeter (DSC) of PAP-1:

A DSC curve of PAP-1 is as shown in FIG. 17. It can be seen from FIG. 17 that: the powdery energetic compound PAP-1 in an unloaded state of Embodiment 8 is decomposed at 375° C., and releases a large amount of heat (about 4685 J/g).

The Amount of Gas Produced by PAP-1 Per Mole Number

For judgment on products obtained by complete explosion of the energetic material in an oxygen-free environment, according to a document (*J. Am. Chem. Soc.* 2012, 134, 1422; *J. Phys. Chem. A.* 2014, 118, 4575; *Chem. Eur. J.* 2016, 22, 1141), final decomposition products include gaseous substances such as nitrogen, halogen hydride, water and carbon dioxide, and solid substances such as metal chlorides and elemental carbon (if oxygen atoms are not enough to completely convert all carbon atoms into the carbon dioxide). Therefore, 1 mole of PAP-1 may produce 11.5 moles of gas substances after complete explosion in the oxygen-free environment, with 0.5 moles of elemental carbon and 1 mole of solid sodium chloride remaining. Under a condition that an enough amount of oxidant (such as commonly used $NH_4ClO_4$) is mixed, PAP-1 per mole produces 1 mole of solid sodium chloride residues after complete explosion.

Embodiment 9

Synthesis and test of $(C_4H_{12}N_2)[NH_4(ClO_4)_3]$

Synthesis Method 1:
1) adding 0.8 mL of ammonia water into 0.9 mL of a perchloric acid solution at a mass fraction of 70 to 72 percent, stirring the mixture at a normal temperature for 5 minutes, and then adding 1.6 mL of the perchloric acid solution at the mass fraction of 70 to 72 percent;
2) adding a proper amount of water into 0.87 g of piperazine, and stirring at the normal temperature to dissolve the piperazine;
3) mixing the solutions obtained in steps 1) and 2); heating the mixture to concentrate it; and stirring the concentrated mixture for 30 minutes; filtering the mixture, and washing residues with ethanol for three times; and performing vacuum drying on the washed residues to obtain a white powdery solid that is identified as perovskite type compound $(C_4H12N_2)[NH_4(ClO_4)_3]$ (No. PAP-4) with the yield of about 40 percent.

Synthesis Method 2:
1) adding 1.72 g of piperazine into 5 mL of water, then adding 5.74 g of a perchloric acid solution at a mass fraction of 70 to 72 percent, and stirring the mixture at a normal temperature for 5 minutes;
2) adding 2.35 g of ammonium perchlorate into 15 mL of water, and then stirring at the normal temperature to dissolve the ammonium perchlorate;
3) mixing the solutions obtained in steps 1) and 2), stirring the mixture for 30 minutes, and then filtering the mixture, washing residues with ethanol for three times, and performing vacuum drying on the washed residues to obtain a white powdery solid which is identified as perovskite type compound $(C_4H_{12}N_2)[NH_4(ClO_4)_3]$ (PAP-4) with a yield of about 80 percent.

Figure 18:
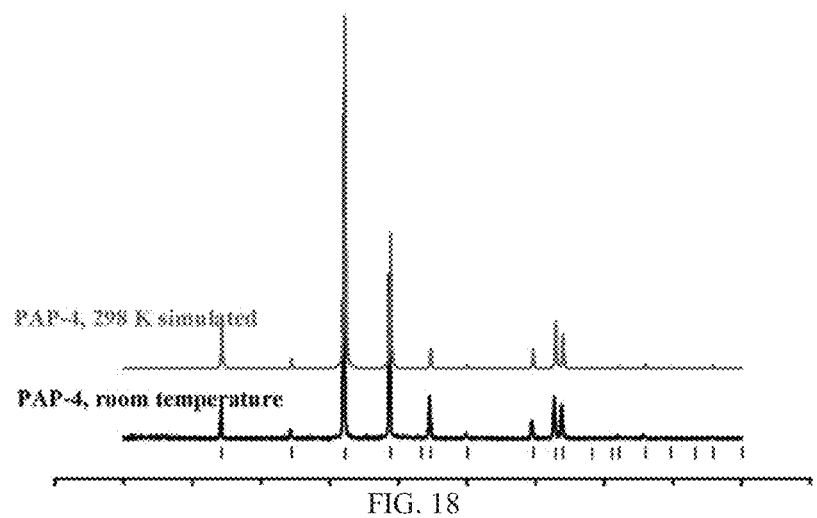
FIG. 18 is a powder X-ray diffraction diagram of energetic compound PAP-4 according to Embodiment 9.

A Powder X-Ray Diffraction Identification Diagram:
The powder X-ray diffraction diagram at the room temperature is as shown in FIG. 18.

Single-Crystal Structure Characterization Test:
Detailed crystal test data are as shown in Table 15.

TABLE 15

Single-crystal X-ray crystallographic data for PAP-4

| Complex | PAP-4 |
|---|---|
| Formula | $C_4H_{16}Cl_3N_3O_{12}$ |
| Formula weight | 404.55 |
| T/K | 298(2) |
| λ/Å | 1.54184 |
| Crystal system | cubic |
| Space group | Fm-3c |
| a/Å | 14.5631(3) |
| V/Å$^3$ | 3088.60(19) |
| Z | 8 |
| $D_c$/g cm$^{-3}$ | 1.737 |
| reflections | 3025 |
| unique reflections | 143 |
| $R_{int}$ | 0.0889 |
| $R_1$ [I > 2σ(I)][a] | 0.0711 |
| $wR_2$ [I > 2σ(I)][b] | 0.2570 |
| $R_1$ (all data) | 0.0733 |
| $wR_2$ (all data) | 0.2647 |
| GOF on $F^2$ | 1.242 |
| Completeness | 1.00 |

[a]$R_1 = \Sigma||F_o| - |F_c||/\Sigma|F_o|$, [b]$wR_2 = \{\Sigma w[(F_o)^2 - (F_c)^2]^2/\Sigma w[(F_o)^2]\}^{1/2}$.

Figure 19:
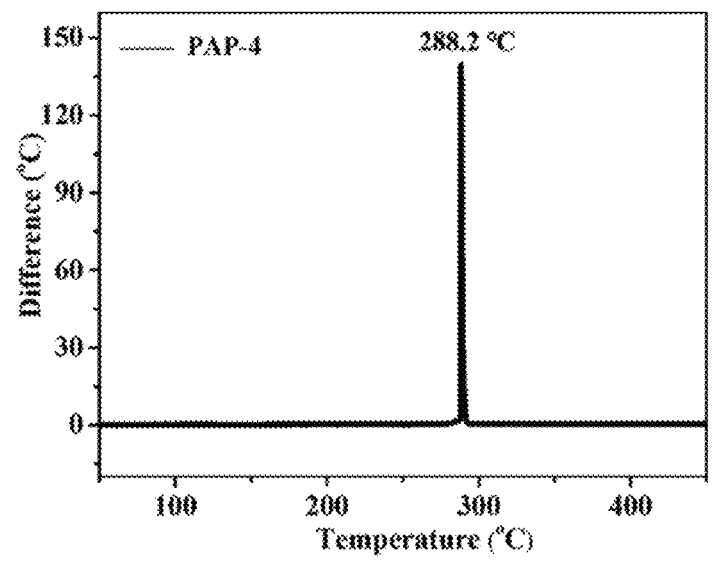
FIG. 19 is a differential thermal analysis curve of energetic compound PAP-4 according to Embodiment 9.

Differential Thermal Analysis (DTA) of PAP-4:
A DTA curve of PAP-4 is as shown in FIG. 19. It can be seen from FIG. 19 that: the powdery energetic compound PAP-4 in an unloaded state of Embodiment S2 decomposes at 288.2° C.

Detonation Heat, Detonation Pressure and Detonation Velocity Values of the Energetic Compound PAP-4 Obtained Theoretically by the DFT:
A decomposition heat value (decomposition enthalpy value $\Delta H_{det}$) of PAP-4 is about 1.43 kcal/g calculated on the basis of the DFT (J. Am. Chem. Soc. 2012, 134, 1422), which is higher than those of active-duty energetic materials HMX (1.26 kcal/g) and RDX (1.27 kcal/g). An energy density is 2.47 kcal/cm$^3$ obtained by conversion of a crystal density at 298 K, which is also higher than those of the active-duty energetic materials HMX (2.38 kcal/cm$^3$) and RDX (2.29 kcal/cm$^3$). According to a Kamlet-Jacob formula, PAP-4 has the detonation velocity of about 8.63 km/s and the detonation pressure of about 32.4 GPa.

Figure 20:
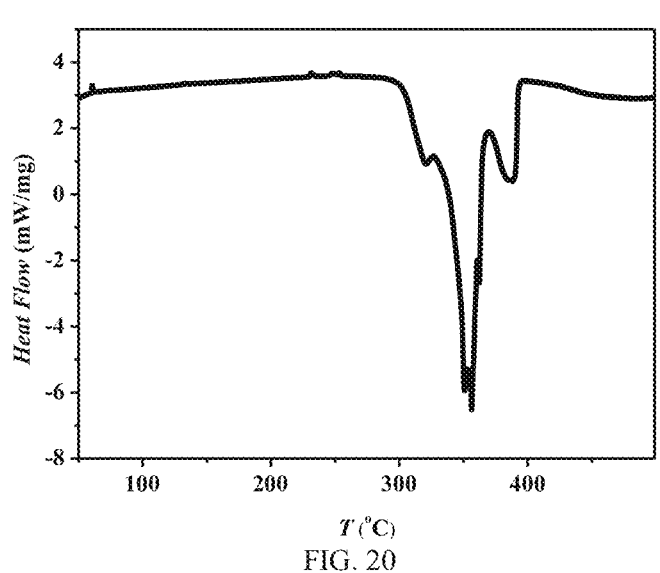
FIG. 20 is a differential scanning calorimetry graph of energetic compound PAP-4 according to Embodiment 9.

Differential Scanning Calorimeter (DSC) of PAP-4:
A DSC curve of PAP-4 is as shown in FIG. 20. It can be seen from FIG. 20 that: the powdery energetic compound PAP-4 in an unloaded state of Embodiment 9 is decomposed at 356° C. (released heat is about 3780 J/g).

The Amount of Gas Produced by PAP-4 Per Mole Number
For judgment on products obtained by complete explosion of the energetic material in an oxygen-free environment, according to a document (J. Am. Chem. Soc. 2012, 134, 1422; J. Phys. Chem. A. 2014, 118, 4575; Chem. Eur. J. 2016, 22, 1141), final decomposition products include gaseous substances such as nitrogen, halogen hydride, water and carbon dioxide, and solid substances such as metal chlorides and elemental carbon (if oxygen atoms are not enough to completely convert all carbon atoms into the carbon dioxide). Therefore, 1 mole of PAP-4 may produce 13.75 moles of gas substances after complete explosion in the oxygen-free environment, with 1.25 moles of elemental carbon remaining. Under a condition that an enough amount of oxidant (such as commonly used $NH_4ClO_4$) is mixed, PAP-4 per mole produces no solid residues after complete explosion.

Embodiment 10

Synthesis and test of $(C_6H_{14}N_2)[K(NO_3)_3]$

Synthesis Method:
1) adding 1.12 g of 1,4-diazabicyclo[2.2.2]octane into a proper amount of water, then adding 1.4 mL of a nitric acid solution at a mass fraction of 65 percent, and stirring the mixture at a normal temperature for 5 minutes;
2) adding 1.01 g of potassium nitrate into a proper amount of water, and stirring the mixture at the normal temperature to dissolve the potassium nitrate;
3) mixing the solutions obtained in steps 1) and 2), stirring and filtering the mixture, washing residues with ethanol for three times, and performing vacuum drying on the washed residues to obtain a white powdery solid that is identified as perovskite type compound $(C_6H_{14}N_2)[K(NO_3)_3]$(No. DAN-2) at the yield of about 50 percent.

Figure 21:
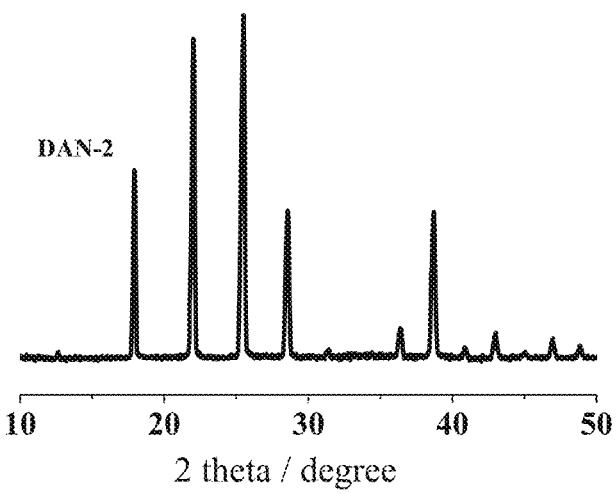
FIG. 21 is a powder X-ray diffraction diagram of energetic compound DAN-2 according to Embodiment 10.

A Powder X-Ray Diffraction Identification Diagram:
The powder X-ray diffraction diagram at the room temperature is as shown in FIG. 21, and its characteristic peak values are as shown in Table 16.

TABLE 16

Characteristic peak values of powder X-ray diffraction of DAN-2

| 2θ/° | d/Å |
|---|---|
| 12.6 | 7.01 |
| 17.9 | 4.94 |
| 22.0 | 4.03 |
| 25.5 | 3.49 |
| 28.6 | 3.12 |

TABLE 16-continued

Characteristic peak values
of powder X-ray diffraction of DAN-2

| 2θ/° | d/Å |
| --- | --- |
| 31.3 | 2.85 |
| 36.4 | 2.47 |
| 38.7 | 2.32 |
| 40.9 | 2.21 |
| 43.0 | 2.10 |

Single-Crystal Structure Characterization Test:
Detailed crystal test data are as shown in Table 17.

TABLE 17

Single-crystal X-ray crystallographic data for DAN-2

| Complex | DAN-2 |
| --- | --- |
| Formula | $C_6H_{14}N_5KO_9$ |
| Formula weight | 339.32 |
| Temperature (K) | 298(2) |
| Crystal system | Cubic |
| Space group | Pm-3m |
| a/Å | 6.9512(1) |
| V/Å$^3$ | 335.88(2) |
| Z | 1 |
| $D_c$/g cm$^{-3}$ | 1.678 |
| reflections collected | 1919 |
| unique reflections | 102 |
| $R_{int}$ | 0.0684 |
| $R_1$ [I > 2σ(I)][a] | 0.0648 |
| $wR_2$ [I > 2σ(I)][b] | 0.1700 |
| $R_1$ (all data) | 0.0649 |
| $wR_2$ (all data) | 0.1702 |
| GOF on F$^2$ | 1.046 |
| Completeness (data) | 0.989 |

[a]$R_1 = \Sigma||F_o| - |F_c||/\Sigma|F_o|$, [b]$wR_2 = \{\Sigma[w(F_o)^2 - (F_c)^2]^2/\Sigma w[(F_o)^2]\}^{1/2}$.

Figure 22:
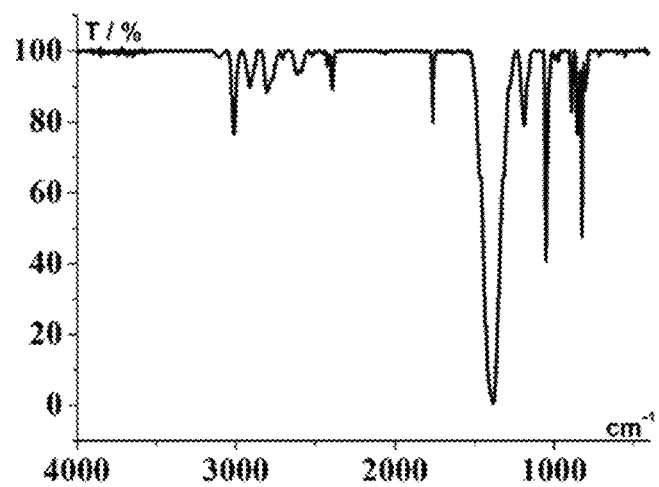
FIG. 22 is an infrared spectrogram of energetic compound DAN-2 according to Embodiment 10.

Infrared Spectral Characterization of DAN-2:
An infrared spectrum of DAN-2 is as shown in FIG. 22. It can be seen from FIG. 22 that: characteristic peaks of a nitrate radical are asymmetric stretching vibration 1385 cm$^{-1}$ and asymmetric bending vibration 852 cm$^{-1}$.

Figure 23:
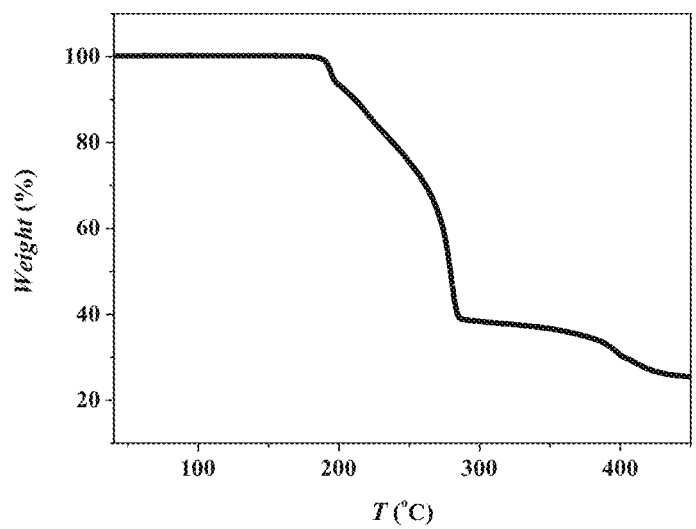
FIG. 23 is a thermogravimetric analysis graph of energetic compound DAN-2 according to Embodiment 10.

Thermal Stability Characterization of DAN-2:
A thermogravimetric curve of DAN-2 is as shown in FIG. 23. It can be seen from FIG. 23 that: under conditions that a sample loading amount is 3.33 mg and a heating rate is 5° C./min, the energetic compound DAN-2 of Embodiment 10 starts to be decomposed at 177° C.

Figure 24:
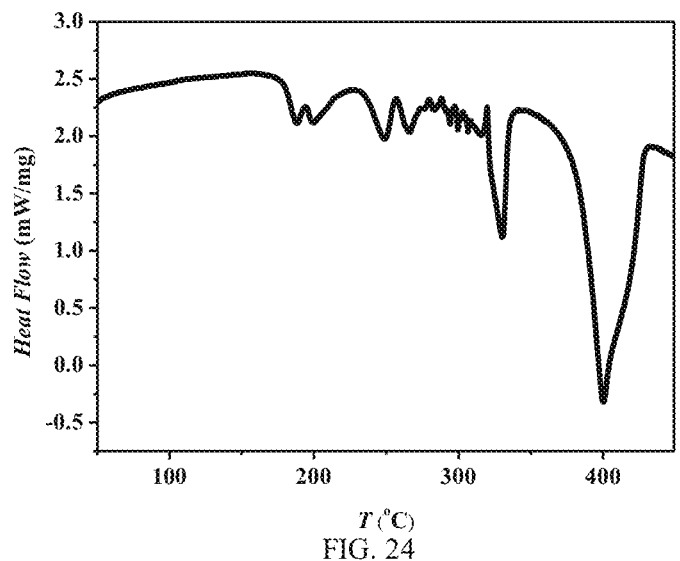
FIG. 24 is a differential scanning calorimetry graph of energetic compound DAN-2 according to Embodiment 10.

Differential Scanning Calorimeter (DSC) of DAN-2:
A DSC curve of DAN-2 is as shown in FIG. 24. It can be seen from FIG. 24 that: the powdery energetic compound DAN-2 in an unloaded state of Embodiment 10 is gradually decomposed at 177° C. (released heat is about 1222 J/g).

Impact and Friction Sensitivity Characterization of DAN-2:
According to a test method of a Federal Institute for Material Research and Testing (BAM), the impact sensitivity of DAN-2 is about 29 J, and the friction sensitivity is about 360 N.

Embodiment 11

Synthesis and test of $(C_6H_{14}N_2)[NH_4(NO_3)_3]$

Synthesis Method:
1) adding 2.0 mL of a nitric acid solution at a mass fraction of 65 percent into 0.78 mL of ammonia water at a mass fraction of 28 percent, and stirring the mixture at a normal temperature;
2) adding 1.14 g of 1,4-diazabicyclo[2.2.2]octane into a proper amount of water, and stirring the mixture at the normal temperature to dissolve the 1,4-diazabicyclo[2.2.2]octane;
3) mixing the solutions obtained in steps 1) and 2), stirring and filtering, washing residues with ethanol for three times, and performing vacuum drying on the washed residues to obtain a white powdery solid that is identified as hexagonal perovskite type compound $(C_6H_{14}N_2)[NH_4(NO_3)_3]$(No. DAN-4) with the yield of about 60 percent.

Figure 25:
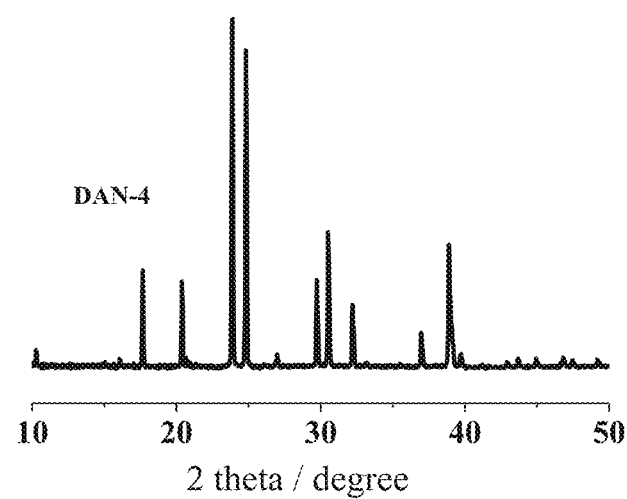
FIG. 25 is a powder X-ray diffraction diagram of energetic compound DAN-4 according to Embodiment 11.

A Powder X-Ray Diffraction Identification Diagram:
The powder X-ray diffraction diagram at the room temperature is as shown in FIG. 25, and its characteristic peak values are as shown in Table 18.

TABLE 18

Characteristic peak values
of powder X-ray diffraction of DAN-4

| 2θ/° | d/Å |
| --- | --- |
| 10.3 | 8.60 |
| 17.7 | 5.02 |
| 20.4 | 4.35 |
| 23.9 | 3.72 |
| 24.8 | 3.58 |
| 27.0 | 3.30 |
| 29.7 | 3.00 |
| 30.5 | 2.93 |
| 32.2 | 2.78 |
| 37.0 | 2.43 |

Single-Crystal Structure Characterization Test:
Detailed crystal test data are as shown in Table 19.

TABLE 19

Single-crystal X-ray crystallographic data for DAN-4

| Complex | DAN-4 |
| --- | --- |
| Formula | $C_6H_{18}N_6O_9$ |
| Formula weight | 318.26 |
| Temperature (K) | 173(2) |
| Crystal system | Hexagonal |
| Space group | P-62c |
| a/Å | 10.0879(1) |
| c/Å | 7.1304(1) |
| V/Å$^3$ | 628.41(2) |
| Z | 2 |
| $D_c$/g cm$^{-3}$ | 1.682 |
| reflections collected | 10135 |
| unique reflections | 484 |
| $R_{int}$ | 0.0825 |
| $R_1$ [I > 2σ(I)][a] | 0.0395 |
| $wR_2$ [I > 2σ(I)][b] | 0.1235 |
| $R_1$ (all data) | 0.0395 |
| $wR_2$ (all data) | 0.1235 |
| GOF on F$^2$ | 1.211 |
| Completeness (data) | 1.000 |

Figure 26:
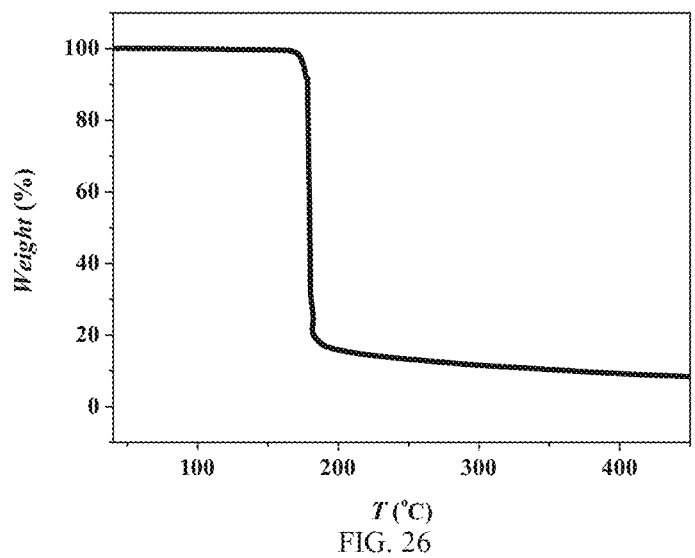
FIG. 26 is a thermogravimetric analysis graph of energetic compound DAN-4 according to Embodiment 11.

[a]$R_1 = \Sigma||F_o| - |F_c||/\Sigma|F_o|$, [b]$wR_2 = \{\Sigma[w(F_o)^2 - (F_c)^2]^2/\Sigma w[(F_o)^2]\}^{1/2}$ Thermal Stability Characterization of DAN-4:
A thermogravimetric curve of DAN-4 is as shown in FIG. 26. It can be seen from FIG. 26 that: under conditions that a sample loading amount is 6.42 mg and a heating rate is 5° C./min, the energetic compound DAN-4 of Embodiment 11 starts to be decomposed at 167° C.

Figure 27:
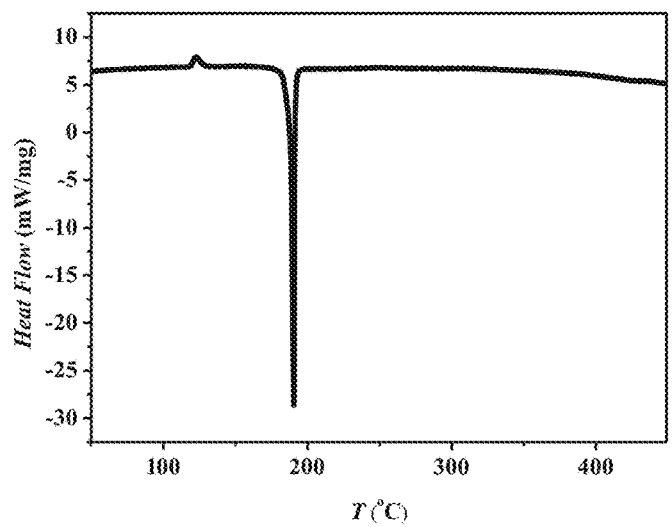
FIG. 27 is a differential scanning calorimetry graph of energetic compound DAN-4 according to Embodiment 11.

Differential Scanning Calorimeter (DSC) of DAN-4:
A DSC curve of DAN-4 is as shown in FIG. 27. It can be seen from FIG. 27 that: the powdery energetic compound DAN-4 in an unloaded state of Embodiment 11 starts to be decomposed at 170° C. (released heat is about 1098 J/g).

The Amount of Gas Produced by DAN-4 Per Mole Number

For judgment on products obtained by complete explosion of the energetic material in an oxygen-free environment, according to a document (J. Am. Chem. Soc. 2012, 134, 1422; J. Phys. Chem. A. 2014, 118, 4575; Chem. Eur. J. 2016, 22, 1141), final decomposition products include gaseous substances such as nitrogen and water, and solid substances such as elemental carbon (considering that oxygen atoms are preferentially combined with hydrogen atoms to form water). Therefore, 1 mole of DAN-4 may produce 12 moles of gas substances after complete explosion in the oxygen-free environment, with 6 moles of elemental carbon remaining. Under a condition that an enough amount of oxidant (such as commonly used $NH_4NO_3$) is mixed, DAN-4 per mole produces no solid residues after complete explosion. Particularly, without halogen elements, DAN-4 does not produce hydrogen halide gas after explosion, thereby reducing characteristic signals in actual application, and relieving environmental pollution.

Embodiment 12

Synthesis and test of $(C_4H_{12}N_2)[K(ClO_4)_3]$ (PAP-2)

Synthesis Method:
1) adding 1.72 g of piperazine into 100 mL of water, then adding 5.74 g of a perchloric acid solution at a mass fraction of 70 to 72 percent, and stirring the mixture at a normal temperature for 5 minutes;
2) adding 2.77 of potassium perchlorate into 100 mL of water, and then heating and stirring the mixture to dissolve the potassium perchlorate.
3) mixing the solutions obtained in steps 1) and 2), stirring the mixture for 30 minutes, filtering the mixture, washing residues with ethanol for three times, and performing vacuum drying on washed residues to obtain a white powdery solid that is identified as perovskite type compound $(C_4H_{12}N_2)[K(ClO_4)_3]$ (PAP-2) with the yield of about 70 percent.

Figure 28:
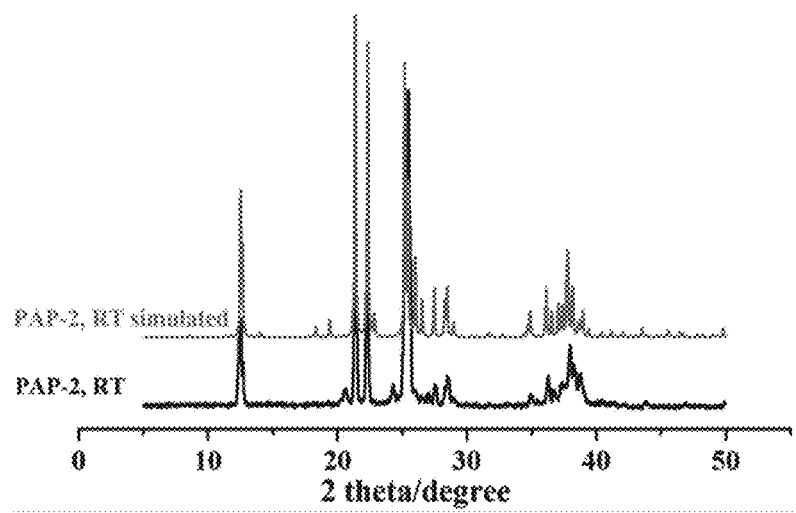
FIG. 28 is a powder X-ray diffraction diagram of energetic compound PAP-2 according to Embodiment 12.

A Powder X-Ray Diffraction Identification Diagram:

The powder X-ray diffraction diagram at the room temperature is as shown in FIG. 28, and its characteristic peak values are as shown in Table 20.

TABLE 20

Characteristic peak values of Powder X-ray diffraction of PAP-2

| $2\theta/°$ | d/Å |
|---|---|
| 12.52 | 7.06 |
| 21.36 | 4.16 |
| 22.32 | 3.98 |
| 25.20 | 3.53 |
| 25.46 | 3.50 |
| 26.00 | 3.42 |
| 26.12 | 3.48 |
| 27.50 | 3.25 |
| 37.78 | 2.38 |
| 38.14 | 2.36 |

Single-Crystal Structure Characterization Test:

Detailed crystal test data are as shown in Table 21.

TABLE 21

Single-crystal X-ray crystallographic data for PAP-2

| Complex | PAP-2 |
|---|---|
| Formula | $C_4H_{12}KCl_3N_2O_{12}$ |
| Formula weight | 425.61 |
| T/K | 284(17) |
| $\lambda$/Å | 1.54178 |
| Crystal system | Orthorhombic |
| Space group | Pbcm |
| a/Å | 10.3353(6) |
| b/Å | 9.6777(6) |
| c/Å | 13.986(1) |
| V/Å$^3$ | 1398.9(2) |
| Z | 4 |
| $D_c$/g cm$^{-3}$ | 2.021 |
| reflections collected | 7003 |
| unique reflections | 1317 |
| $R_{int}$ | 0.0715 |
| $R_1$ [I > 2σ(I)]$^{[a]}$ | 0.0704 |
| $wR_2$ [I > 2σ(I)]$^{[b]}$ | 0.1849 |
| $R_1$ (all data) | 0.0804 |
| $wR_2$ (all data) | 0.1998 |
| GOF on $F^2$ | 1.056 |

Figure 29:
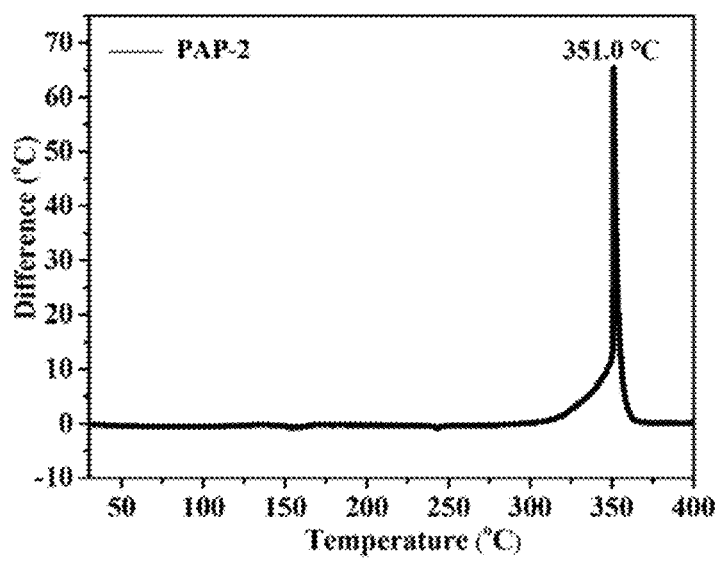
FIG. 29 is a differential thermal analysis curve of energetic compound PAP-2 according to Embodiment 12.

$^{[a]}R_1 = \Sigma||F_o| - |F_c||/\Sigma|F_o|$, $^{[b]}wR_2 = \{\Sigma w[(F_o)^2 - (F_c)^2]^2/\Sigma w[(F_o)^2]\}^{1/2}$;

Differential Thermal Analysis (DTA) of PAP-2:

A DTA curve of PAP-2 is as shown in FIG. 29. It can be seen from FIG. 29 that: the powdery energetic compound PAP-2 in an unloaded state of Embodiment 1 is decomposed at 351.0° C.

Detonation Heat, Detonation Pressure and Detonation Velocity Values of the Energetic Compound PAP-2 Obtained Theoretically by the DFT:

A decomposition heat value (decomposition enthalpy value $\Delta H_{det}$) of PAP-2 is about 1.50 kcal/g calculated on the basis of the DFT (J. Am. Chem. Soc. 2012, 134, 1422), which is higher than those of active-duty energetic materials HMX (1.26 kcal/g) and RDX (1.27 kcal/g). An energy density is 3.03 kcal/cm$^3$ obtained by conversion of a crystal density at 284 K, which is also higher than those of the active-duty energetic materials HMX (2.38 kcal/cm$^3$) and RDX (2.29 kcal/cm$^3$). According to a Kamlet-Jacob formula, PAP-2 has the detonation velocity of about 8.78 km/s and the detonation pressure of about 36.6 GPa.

The Amount of Gas Produced by PAP-2 Per Mole Number

For judgment on products obtained by complete explosion of the energetic material in an oxygen-free environment, according to a document (J. Am. Chem. Soc. 2012, 134, 1422; J. Phys. Chem. A. 2014, 118, 4575; Chem. Eur. J. 2016, 22, 1141), final decomposition products include gaseous substances such as nitrogen, halogen hydride, water and carbon dioxide, and solid substances such as metal chlorides and elemental carbon (if oxygen atoms are not enough to completely convert all carbon atoms into the carbon dioxide). Therefore, 1 mole of PAP-2 may produce 11.5 moles of gas substances after complete explosion in the oxygen-free environment, with 0.5 moles of elemental carbon and 1 mole of solid potassium chloride remaining. Under a condition that an enough amount of oxidant (such as commonly used $NH_4ClO_4$) is mixed, PAP-2 per mole produces 1 mole of solid potassium chloride residues after complete explosion.

Embodiment 13

Synthesis and test of $(C_6H_{14}N_2O)[NH_4(ClO_4)_3]$ (DAP-O4)

Synthesis Method:
1) putting 2.24 g of 1,4-diazabicyclo[2.2.2]octane into a flask, gradually and slowly adding 5.9 mL of hydrogen peroxide at a mass fraction of 30 percent at 0° C. for 5 min and then warmed to room temperature. The reaction mixture was gently heated to 30° C. for 5 min (monitoring the reaction temperature to prevent a drastic exothermic reaction), thus obtaining an aqueous solution of 1,4-diazabicyclo[2.2.2]octane 1-oxide, then adding 5.75 g of a perchloric acid solution at a mass fraction of 70 to 72 percent, and stirring the mixture for 20 minutes;
2) adding 2.35 g of ammonium perchlorate into 15 mL of water, and then stirring at the normal temperature to dissolve the ammonium perchlorate;
3) mixing the solutions obtained in steps 1) and 2), stirring the mixture for 30 minutes, and then filtering the mixture, washing residues with ethanol for three times, and performing vacuum drying on the washed residues to obtain a white powdery solid which is identified as perovskite type compound $(C_6H_{14}N_2O)[NH_4(ClO_4)_3]$ (DAP-O4) with a yield of about 85 percent.

Figure 30:
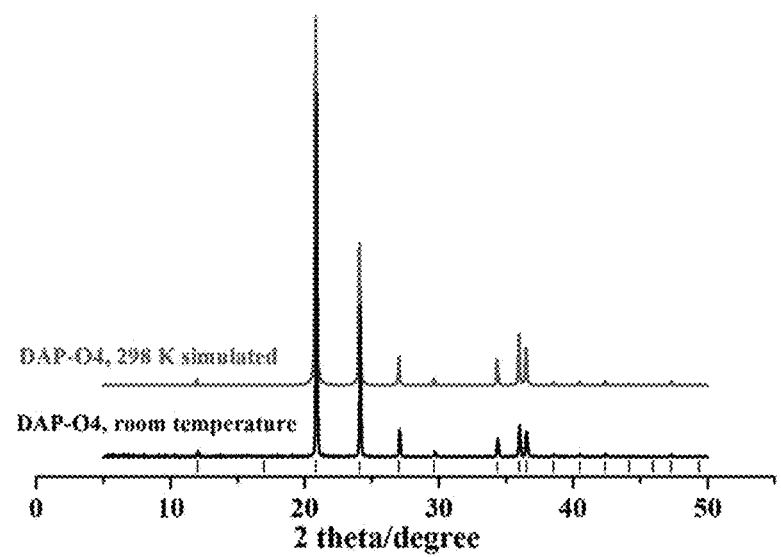
FIG. 30 is a powder X-ray diffraction diagram of energetic compound DAP-O4 according to Embodiment 13.

A Powder X-Ray Diffraction Identification Diagram:
The powder X-ray diffraction diagram at the room temperature is as shown in FIG. 30.

Single-Crystal Structure Characterization Test:
Detailed crystal test data are as shown in Table 22.

TABLE 22

Single-crystal X-ray crystallographic data for DAP-O4

| Complex | DAP-O4 |
|---|---|
| Formula | $C_6H_{18}Cl_3N_3O_{13}$ |
| Formula weight | 446.55 |
| T/K | 298(2) |
| λ/Å | 1.54178 |
| Crystal system | Cubic |
| Space group | Fm-3c |
| a/Å | 14.76270(10) |
| V/Å$^3$ | 3217.34(7) |
| Z | 8 |
| $D_c$/g cm$^{-3}$ | 1.844 |
| reflections collected | 5939 |
| unique reflections | 168 |
| $R_{int}$ | 0.0373 |
| $R_1$ [I > 2σ(I)]$^{[a]}$ | 0.0298 |
| $wR_2$ [I > 2σ(I)]$^{[b]}$ | 0.0852 |
| $R_1$ (all data) | 0.0306 |
| $wR_2$ (all data) | 0.0860 |
| GOF on F$^2$ | 1.151 |
| Completeness | 1.00 |

$^{[a]}R_1 = \Sigma||F_o| - |F_c||/\Sigma|F_o|$, $^{[b]}wR_2 = \{\Sigma w[(F_o)^2 - (F_c)^2]^2/\Sigma w[(F_o)^2]\}^{1/2}$.

Figure 31:
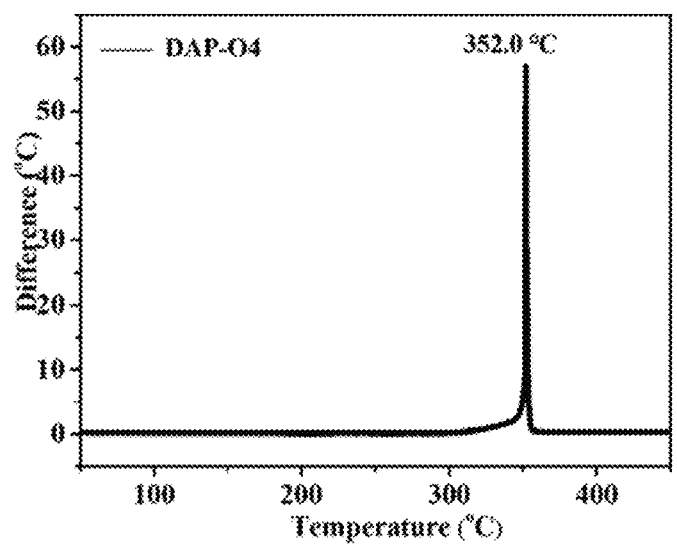
FIG. 31 is a differential thermal analysis curve of energetic compound DAP-O4 according to Embodiment 13.

Differential Thermal Analysis (DTA) of DAP-O4:
A DTA curve of DAP-O4 is as shown in FIG. 31. It can be seen from FIG. 31 that: the powdery energetic compound DAP-O4 in an unloaded state of Embodiment S3 decomposes at 352.0° C.

Impact and Friction Sensitivity Characterization of DAP-O4:
According to a test method of a Federal Institute for Material Research and Testing (BAM), the impact sensitivity of DAP-O4 is about 17.5 J, and the friction sensitivity is about 5 N.

Detonation Heat, Detonation Pressure and Detonation Velocity Values of the Energetic Compound DAP-O4 Obtained Theoretically by the DFT:
A decomposition heat value (decomposition enthalpy value $\Delta H_{det}$) of DAP-O4 is about 1.48 kcal/g calculated on the basis of the DFT (J. Am. Chem. Soc. 2012, 134, 1422), which is higher than those of active-duty energetic materials HMX (1.26 kcal/g) and RDX (1.27 kcal/g). An energy density is 2.73 kcal/cm$^3$ obtained by conversion of a crystal density at 298 K, which is also higher than those of the active-duty energetic materials HMX (2.38 kcal/cm$^3$) and RDX (2.29 kcal/cm$^3$). According to a Kamlet-Jacob formula, PAP-M4 has the detonation velocity of about 8.90 km/s and the detonation pressure of about 35.7 GPa.

The Amount of Gas Produced by DAP-O4 Per Mole Number

For judgment on products obtained by complete explosion of the energetic material in an oxygen-free environment, according to a document (J. Am. Chem. Soc. 2012, 134, 1422; J. Phys. Chem. A. 2014, 118, 4575; Chem. Eur. J. 2016, 22, 1141), final decomposition products include gaseous substances such as nitrogen, halogen hydride, water and carbon dioxide, and solid substances such as elemental carbon (if oxygen atoms are not enough to completely convert all carbon atoms into the carbon dioxide). Therefore, 1 mole of DAP-O4 may produce 14.75 moles of gas substances after complete explosion in the oxygen-free environment, with 3.25 moles of elemental carbon. Under a condition that an enough amount of oxidant (such as commonly used $NH_4ClO_4$) is mixed, DAP-O4 produces no solid residues after complete explosion.

Embodiment 14

Synthesis and test of $(C_5H_{14}N_2)[NH_4(ClO_4)_3]$ (PAP-M4)

Synthesis Method:
1) adding 2.00 g of 1-methyl-piperazine into 5 mL of water, then adding 5.74 g of a perchloric acid solution at a mass fraction of 70 to 72 percent, and stirring the mixture at a normal temperature for 5 minutes;
2) adding 2.35 g of ammonium perchlorate into 15 mL of water, and then stirring at the normal temperature to dissolve the ammonium perchlorate;
3) mixing the solutions obtained in steps 1) and 2), stirring the mixture for 30 minutes, and then filtering the mixture, washing residues with ethanol for three times, and performing vacuum drying on the washed residues to obtain a white powdery solid which is identified as perovskite type compound $(C_5H_{14}N_2)[NH_4(ClO_4)_3]$ (PAP-M4) with a yield of about 80 percent.

Figure 32:
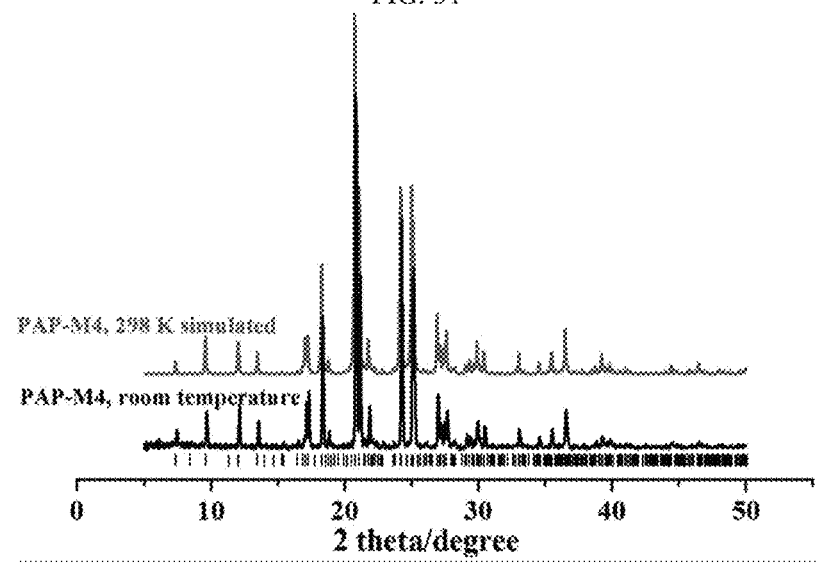
FIG. 32 is a powder X-ray diffraction diagram of energetic compound PAP-M4 according to Embodiment 14.

A Powder X-Ray Diffraction Identification Diagram:
The powder X-ray diffraction diagram at the room temperature is as shown in FIG. 32.

Single-Crystal Structure Characterization Test:
Detailed crystal test data are as shown in Table 23.

TABLE 23

Single-crystal X-ray crystallographic data for PAP-M4

| Complex | PAP-M4 |
|---|---|
| Formula | $C_5H_{18}Cl_3N_3O_{12}$ |
| Formula weight | 418.57 |
| T/K | 298(2) |

TABLE 23-continued

Single-crystal X-ray crystallographic data for PAP-M4

| Complex | PAP-M4 |
|---|---|
| $\lambda$/Å | 1.54178 |
| Crystal system | orthorhombic |
| Space group | Pnma |
| a/Å | 10.26733(15) |
| b/Å | 14.7004(2) |
| c/Å | 20.9914(3) |
| V/Å$^3$ | 3168.32(8) |
| Z | 8 |
| $D_c$/g cm$^{-3}$ | 1.755 |
| reflections collected | 15561 |
| unique reflections | 3399 |
| $R_{int}$ | 0.0381 |
| $R_1$ [I > 2σ(I)][a] | 0.0563 |
| $wR_2$ [I > 2σ(I)][b] | 0.1611 |
| $R_1$ (all data) | 0.0593 |
| $wR_2$ (all data) | 0.1633 |
| GOF on F$^2$ | 1.078 |
| Completeness | 1.00 |

[a]$R_1 = \Sigma||F_o| - |F_c||/\Sigma|F_o|$, [b]$wR_2 = \{\Sigma w[(F_o)^2 - (F_c)^2]^2/\Sigma w[(F_o)^2]\}^{1/2}$.

Figure 33:
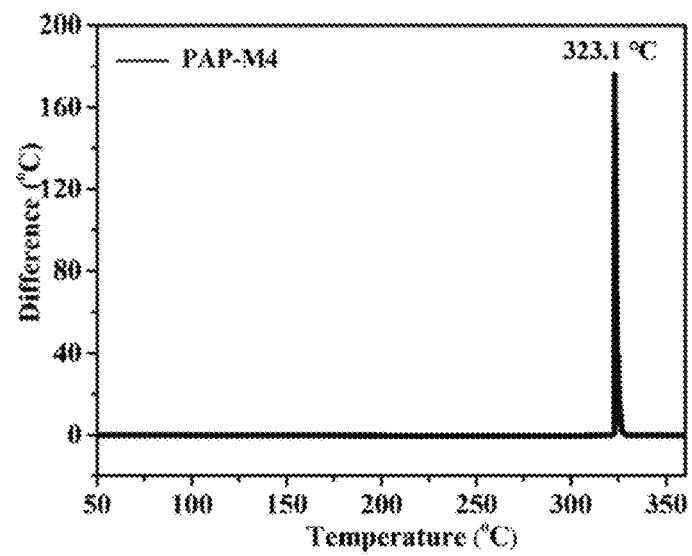
FIG. 33 is a differential thermal analysis curve of energetic compound PAP-M4 according to Embodiment 14.
Figure 34:
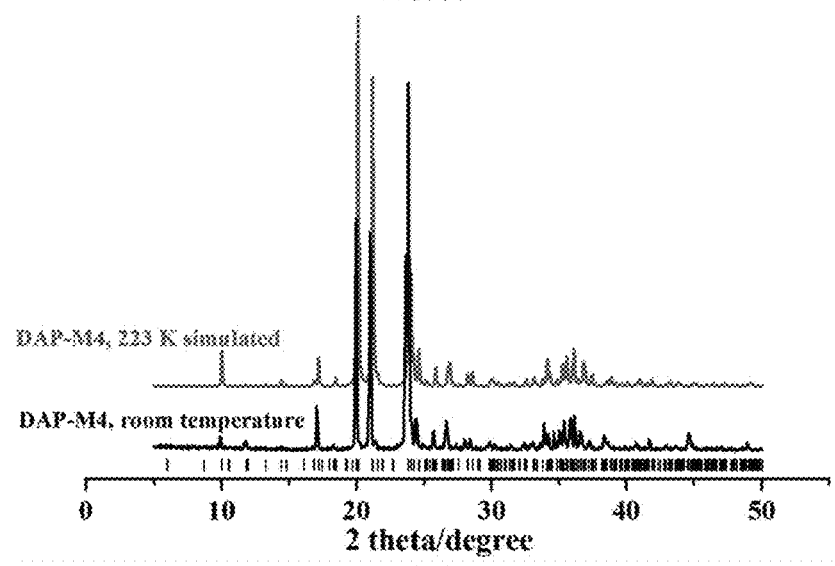
FIG. 34 is a powder X-ray diffraction diagram of energetic compound DAP-M4 according to Embodiment 15.

Differential Thermal Analysis (DTA) of PAP-M4:

A DTA curve of PAP-M4 is as shown in FIG. 33. It can be seen from FIG. 33 that: the powdery energetic compound PAP-M4 in an unloaded state of Embodiment S4 decomposes at 323.1° C.

Impact and Friction Sensitivity Characterization of PAP-M4:

According to a test method of a Federal Institute for Material Research and Testing (BAM), the impact sensitivity of PAP-M4 is about 30 J, and the friction sensitivity is about 6 N.

Detonation Heat, Detonation Pressure and Detonation Velocity Values of the Energetic Compound PAP-M4 Obtained Theoretically by the DFT:

A decomposition heat value (decomposition enthalpy value $\Delta H_{det}$) of PAP-M4 is about 1.23 kcal/g calculated on the basis of the DFT (J. Am. Chem. Soc. 2012, 134, 1422), which is lower than those of active-duty energetic materials HMX (1.26 kcal/g) and RDX (1.27 kcal/g). An energy density is 2.16 kcal/cm$^3$ obtained by conversion of a crystal density at 298 K, which is also lower than those of the active-duty energetic materials HMX (2.38 kcal/cm$^3$) and RDX (2.29 kcal/cm$^3$). According to a Kamlet-Jacob formula, PAP-M4 has the detonation velocity of about 8.63 km/s and the detonation pressure of about 32.4 GPa.

The Amount of Gas Produced by PAP-M4 Per Mole Number

For judgment on products obtained by complete explosion of the energetic material in an oxygen-free environment, according to a document (J. Am. Chem. Soc. 2012, 134, 1422; J. Phys. Chem. A. 2014, 118, 4575; Chem. Eur. J. 2016, 22, 1141), final decomposition products include gaseous substances such as nitrogen, halogen hydride, water and carbon dioxide, and solid substances such as elemental carbon (if oxygen atoms are not enough to completely convert all carbon atoms into the carbon dioxide). Therefore, 1 mole of PAP-M4 may produce 14.25 moles of gas substances after complete explosion in the oxygen-free environment, with 2.75 moles of elemental carbon. Under a condition that an enough amount of oxidant (such as commonly used NH$_4$ClO$_4$) is mixed, PAP-M4 produces no solid residues after complete explosion.

Embodiment 15

Synthesis and test of $(C_7H_{16}N_2)[NH_4(ClO_4)_3]$ (DAP-M4)

Synthesis Method:

1) adding 5.08 g of 1-methyl-1,4-diazabicyclo[2.2.2]octane-1,4-diium iodide (Synthesis, 2007, 24, 3776-3778.) into 5 mL of water, then adding 5.74 g of a perchloric acid solution at a mass fraction of 70 to 72 percent, and stirring the mixture at a normal temperature for 5 minutes;
2) adding 2.35 g of ammonium perchlorate into 15 mL of water, and then stirring at the normal temperature to dissolve the ammonium perchlorate;
3) mixing the solutions obtained in steps 1) and 2), stirring the mixture for 30 minutes, and then filtering the mixture, washing residues with ethanol for three times, and performing vacuum drying on the washed residues to obtain a white powdery solid which is identified as perovskite type compound $(C_7H_{16}N_2)[NH_4(ClO_4)_3]$ with a yield of about 70 percent.

Figure 35:
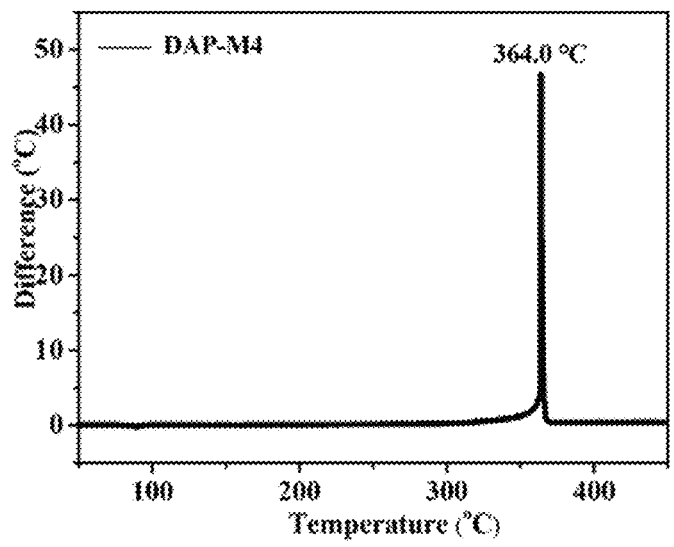
FIG. 35 is a differential thermal analysis curve of energetic compound DAP-M4 according to Embodiment 15.

A Powder X-Ray Diffraction Identification Diagram:

The powder X-ray diffraction diagram at the room temperature is as shown in FIG. 35.

Single-Crystal Structure Characterization Test:

Detailed crystal test data are as shown in Table 24.

TABLE 24

Single-crystal X-ray crystallographic data for DAP-M4

| Complex | DAP-M4 |
|---|---|
| Formula | $C_7H_{20}Cl_3N_3O_{12}$ |
| Formula weight | 444.61 |
| T/K | 223(2) |
| $\lambda$/Å | 0.71073 |
| Crystal system | monoclinic |
| Space group | P2$_1$ |
| a/Å | 10.15203(16) |
| b/Å | 10.9824(2) |
| c/Å | 14.7774(2) |
| β/° | 89.8562(14) |
| V/Å$^3$ | 1647.58(5) |
| Z | 4 |
| $D_c$/g cm$^{-3}$ | 1.792 |
| reflections collected | 27589 |
| unique reflections | 12392 |
| $R_{int}$ | 0.0324 |
| $R_1$ [I > 2σ(I)][a] | 0.0364 |
| $wR_2$ [I > 2σ(I)][b] | 0.0909 |
| $R_1$ (all data) | 0.0414 |
| $wR_2$ (all data) | 0.0952 |
| GOF on F$^2$ | 1.040 |
| Completeness | 0.99 |

[a]$R_1 = \Sigma||F_o| - |F_c||/\Sigma|F_o|$, [b]$wR_2 = \{\Sigma w[(F_o)^2 - (F_c)^2]^2/\Sigma w[(F_o)^2]\}^{1/2}$.

Differential Thermal Analysis (DTA) of DAP-M4:

A DTA curve of DAP-M4 is as shown in FIG. 35. It can be seen from FIG. 35 that: the powdery energetic compound DAP-M4 in an unloaded state of Embodiment S5 decomposes at 364.0° C.

Impact and Friction Sensitivity Characterization of DAP-M4:

According to a test method of a Federal Institute for Material Research and Testing (BAM), the impact sensitivity of DAP-M4 is about 7.5 J, and the friction sensitivity is about 10 N.

Detonation Heat, Detonation Pressure and Detonation Velocity Values of the Energetic Compound DAP-M4 Obtained Theoretically by the DFT:

A decomposition heat value (decomposition enthalpy value $\Delta H_{det}$) of DAP-M4 is about 1.20 kcal/g calculated on the basis of the DFT (*J. Am. Chem. Soc.* 2012, 134, 1422), which is lower than those of active-duty energetic materials HMX (1.26 kcal/g) and RDX (1.27 kcal/g). An energy density is 2.15 kcal/cm$^3$ obtained by conversion of a crystal density at 223 K, which is also lower than those of the active-duty energetic materials HMX (2.38 kcal/cm$^3$) and RDX (2.29 kcal/cm$^3$). According to a Kamlet-Jacob formula, DAP-M4 has the detonation velocity of about 8.08 km/s and the detonation pressure of about 28.8 GPa.

The Amount of Gas Produced by DAP-M4 Per Mole Number

For judgment on products obtained by complete explosion of the energetic material in an oxygen-free environment, according to a document (*J. Am. Chem. Soc.* 2012, 134, 1422; *J. Phys. Chem. A.* 2014, 118, 4575; *Chem. Eur. J.* 2016, 22, 1141), final decomposition products include gaseous substances such as nitrogen, halogen hydride, water and carbon dioxide, and solid substances such as elemental carbon (if oxygen atoms are not enough to completely convert all carbon atoms into the carbon dioxide). Therefore, 1 mole of DAP-M4 may produce 14.75 moles of gas substances after complete explosion in the oxygen-free environment, with 5.25 moles of elemental carbon. Under a condition that an enough amount of oxidant (such as commonly used $NH_4ClO_4$) is mixed, DAP-M4 produces no solid residues after complete explosion.

The perovskite-type energetic compound of the present application features high detonation heat, high energy density, high detonation velocity, high detonation pressure, high safety and extremely low impact, friction and electrostatic sensitivities, with non-volatile, non-decomposed and non-hygroscopic characteristics. The compound can be prepared in batches from cheap and readily-available raw materials through simple synthetic process which gives no by-products.

The perovskite-type energetic compound of the present application can produce some effects which are unexpectable in the prior art when used as energetic materials such as explosives. Although perchlorate anion is an energetic ligand, most of the perchlorate-containing compounds at present cannot be used as practical energetic materials due to various disadvantages (see "*High Energy Materials: Propellants, Explosives and Pyrotechnics*", p. 28, Jai Prakash Agrawal, Wiley-VCH Press, 2010). For example, common perchlorate salts such as sodium perchlorate and lithium perchlorate are highly hygroscopic in nature, and potassium perchlorate was used as a pro-oxidant for flash bombs, but later it was found to have excessive impact sensitivity and easy to explode during transportation. The theoretical detonation heat of ammonium perchlorate, which is still classified as an explosive, is only 1972 J/g, which is far below the detonation heat level of the energetic compound of the present application. However, even if the perovskite-type compound of the present application contains such explosive ligands, it can still maintain the excellent thermal stability and non-hygroscopic characteristic, which makes it an energetic material with high safety and easy storage. At the same time, due to the rich energetic ligands, the alternatively arranged oxidizing energetic anions and reducing organic cations in the space, high crystal density, powerful instantaneous burst capability, high energy density, and high detonation heat, detonation pressure and detonation velocity, the perovskite-type energetic compound, as explosives, has made a great leap in performance compared with the prior art.

The above-mentioned embodiments are preferred embodiments of the present application, but the embodiments of the present application are not limited by the above-mentioned embodiments. Any other variations, modifications, replacements, combinations and simplifications that are made without departing from the spiritual essence and theory of the present application shall all be equivalent substitute modes and fall within the protection scope of the present application.

What is claimed is:

1. A perovskite-type compound of formula:

$ABX_3$, wherein:

(i) A is:

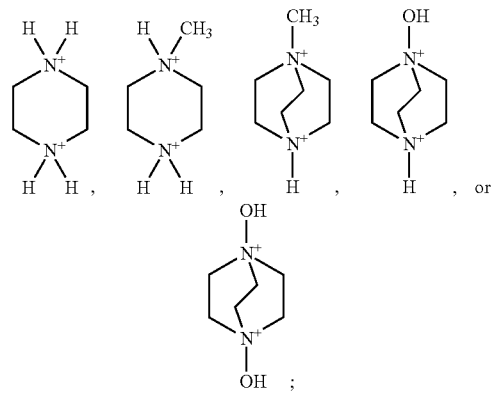

B is Na$^+$, K$^+$, Rb$^+$, or NH$_4^+$; and
X is ClO$_4^-$, IO$_4^-$, or NO$_3^-$; or (ii) A is:

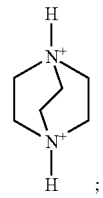

B is Na$^+$, K$^+$, or Rb$^+$; and
X is IO$_4^-$ or NO$_3^-$; or (iii) A is:

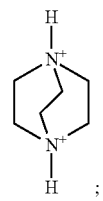

B is NH$_4^+$; and
X is ClO$_4^-$, IO$_4^-$, or NO$_3^-$.

2. The compound of claim 1, wherein A is:

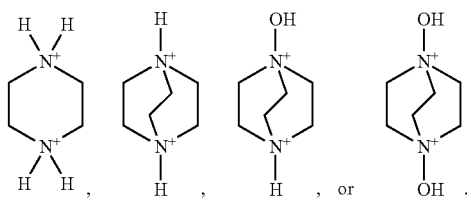 [SMILES: C1C[NH2+]CC[NH2+]1 ; C1C[NH+]2CC[NH+]1CC2 ; O[N+]12CC[NH+](CC1)CC2 ; O[N+]12CC[N+](O)(CC1)CC2]

3. The compound of claim 1, wherein A is:

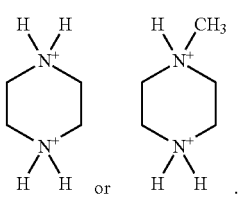

4. The compound of claim 1, wherein A is:

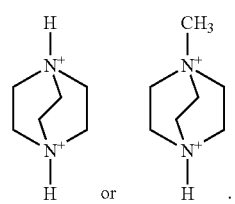

5. The compound of claim 1, wherein A is:

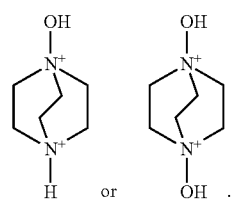 [SMILES: O[N+]12CC[NH+](CC1)CC2 ; O[N+]12CC[N+](O)(CC1)CC2]

6. The compound of claim 1, wherein A is:

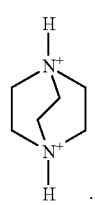

7. The compound of claim 1, wherein B is Na$^+$.
8. The compound of claim 1, wherein B is K$^+$.
9. The compound of claim 1, wherein B is NH$_4^+$.
10. The compound of claim 1, wherein X is ClO$_4^-$.
11. The compound of claim 1, wherein X is IO$_4^-$.

12. The compound of claim 1, wherein:
B is NH$_4^+$; and
X is ClO$_4^-$.

13. The compound of claim 1, wherein:
A is:

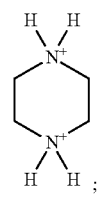

B is NH$_4^+$; and
X is ClO$_4^-$.

14. The compound of claim 1, wherein:
A is:

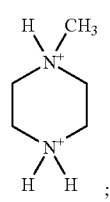

B is NH$_4^+$; and
X is ClO$_4^-$.

15. The compound of claim 1, wherein:
A is:

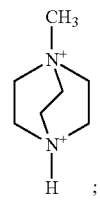

B is NH$_4^+$; and
X is ClO$_4^-$.

16. The compound of claim 1, wherein:
A is:

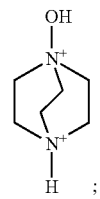

B is NH$_4^+$; and
X is ClO$_4^-$.

17. The compound of claim 1, wherein:
A is:

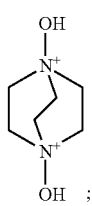

B is $NH_4^+$; and
X is $ClO_4^-$.

18. The compound of claim 1, wherein:
A is:

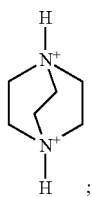

B is $NH_4^+$; and
X is $ClO_4^-$.

19. A process for preparing the compound of claim 1 of formula:

$ABX_3$, wherein:
(i) A is:

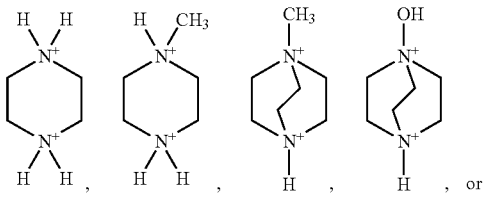

B is $Na^+$, $K^+$, $Rb^+$, or $NH_4^+$; and
X is $ClO_4^-$, $IO_4^-$ or $NO_3^-$; or
(ii) A is:

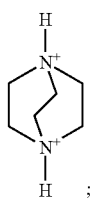

B is $Na^+$, $K^+$, or $Rb^+$; and
X is $IO_4^-$ or $NO_3^-$; or (iii) A is:

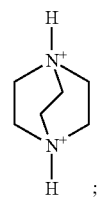

B is $NH_4^+$; and
X is $ClO_4^-$, $IO_4^-$, or $NO_3^-$;
wherein the process comprises the following steps:
(1) adding a $HClO_4$ solution to a solution of

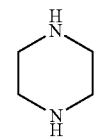

to form a first mixture; and
adding a $Na^+ClO_4^-$ solution to the first mixture; or
(2) adding $NH_3$ to a $HClO_4$ solution to form a second mixture; and
adding a solution of

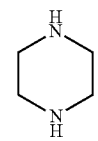

to the second mixture; or
(3) adding a $HClO_4$ solution to a solution of

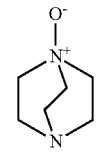

to form a third mixture; and
adding a $K^+ClO_4^-$ solution to the third mixture; or
(4) adding a $HClO_4$ solution to a solution of

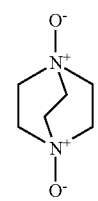

to form a fourth mixture; and
adding a $K^+ClO_4^-$ solution to the fourth mixture; or (5) adding NH₃ to a HClO₄ solution to form a fifth mixture; and
adding a solution of

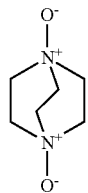

to the fifth mixture; or
(6) adding a HNO₃ solution to a solution of

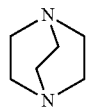

to form a sixth mixture; and
adding a K⁺NO₃⁻ solution to the sixth mixture; or
(7) adding a HClO₄ solution to a solution of

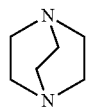

to form a seventh mixture; and
adding a NH₄⁺ClO₄⁻ solution to the seventh mixture; or
(8) adding NH₃ to a HNO₃ solution to form an eighth mixture; and
adding a solution of

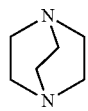

to the eighth mixture.

20. A process for preparing the compound of claim 1 of formula:

ABX₃, wherein:
(i) A is:

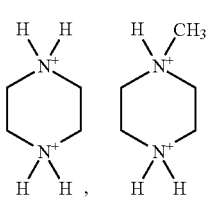 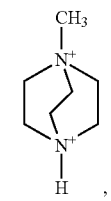 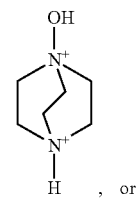 

-continued

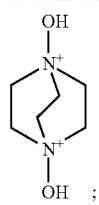

B is Na⁺, K⁺, Rb⁺, or NH₄⁺; and
X is ClO₄⁻, IO₄⁻, or NO₃⁻; or
(ii) A is:

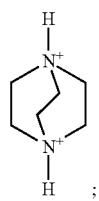

B is Na⁺, K⁺, or Rb⁺; and
X is IO₄⁻ or NO₃⁻; or
(iii) A is:

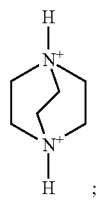

B is NH₄⁺; and
X is ClO₄⁻, IO₄⁻, or NO₃⁻;
wherein the process comprises the following steps:
(9) adding a HClO₄ solution to a solution of

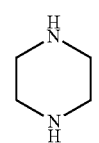

to form a ninth mixture; and
adding a K⁺ClO₄⁻ solution to the ninth mixture; or

(10) adding a HClO₄ solution to a solution of

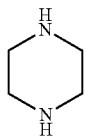

to form a tenth mixture; and
 adding an $NH_4^+ClO_4^-$ solution to the tenth mixture; or
(11) adding a HClO₄ solution to a solution of

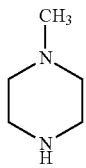

to form an eleventh mixture; and
 adding an $NH_4^+ClO_4^-$ solution to the eleventh mixture; or

(12) adding a HClO₄ solution to a solution of

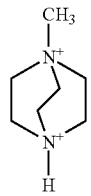

to form a twelfth mixture; and
 adding an $NH_4^+ClO_4^-$ solution to the twelfth mixture; or
(13) adding a HClO₄ solution to a solution of

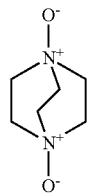

to form a thirteenth mixture; and
 adding an $NH_4^+ClO_4^-$ solution to the thirteenth mixture.

\* \* \* \* \*